US008562505B2

(12) United States Patent  (10) Patent No.: US 8,562,505 B2
Levy et al.  (45) Date of Patent: Oct. 22, 2013

(54) UNIFORM FIELD MAGNETIZATION AND TARGETING OF THERAPEUTIC FORMULATIONS

(75) Inventors: Robert J. Levy, Merion Station, PA (US); Boris Polyak, Philadelphia, PA (US); Michael Chorny, Philadelphia, PA (US); Ivan Alferiev, Clementon, NJ (US); Gennady Friedman, Richboro, PA (US); Darryl Williams, Philadelphia, PA (US); Ilia Fishbein, Philadelphia, PA (US)

(73) Assignees: The Children's Hospital of Philadelphia, Philadelphia, PA (US); Drexel University, Philadelphia, PA (US)

( * ) Notice: Subject to any disclaimer, the term of this patent is extended or adjusted under 35 U.S.C. 154(b) by 951 days.

(21) Appl. No.: 12/150,864

(22) Filed: May 1, 2008

(65) Prior Publication Data

US 2009/0082611 A1  Mar. 26, 2009
US 2013/0096361 A9  Apr. 18, 2013

Related U.S. Application Data

(63) Continuation-in-part of application No. PCT/US2007/009603, filed on Apr. 20, 2007, and a continuation-in-part of application No. 11/250,948, filed on Oct. 14, 2005, now Pat. No. 7,846,201, which is a continuation-in-part of application No. PCT/US2004/011861, filed on Apr. 16, 2004.

(60) Provisional application No. 60/794,191, filed on Apr. 21, 2006, provisional application No. 60/546,233, filed on Feb. 20, 2004, provisional application No. 60/941,058, filed on May 31, 2007.

(51) Int. Cl.
*A61N 2/10* (2006.01)

(52) U.S. Cl.
USPC ...... 600/12; 600/9; 600/13; 600/15; 424/422; 424/426

(58) Field of Classification Search
USPC .................. 128/897; 424/417–426; 607/116; 600/12–15
See application file for complete search history.

(56) References Cited

U.S. PATENT DOCUMENTS 3,474,777 A   10/1969  Figge et al.
4,176,058 A   11/1979  Grobler
(Continued)

FOREIGN PATENT DOCUMENTS

WO   WO 00/43044 A1   7/2000
WO   WO 02/072172    9/2002
(Continued)

OTHER PUBLICATIONS

Zillies and Coester. Evaluating gelatin based nanoparticles as a carrier system for double stranded oligonucleotides. J Pharmaceut Sci. 7(4):17-21, 2004.*

(Continued)

*Primary Examiner* — Christine Matthews
*Assistant Examiner* — Joshua D Lannu
(74) *Attorney, Agent, or Firm* — RatnerPrestia

(57) ABSTRACT

Systems and methods for magnetic targeting of therapeutic particles are provided. Therapeutic particles comprise one or more magnetic or magnetizable materials and at least one therapeutic agent. Therapeutic particles are specifically targeted using uniform magnetic fields capable of magnetizing magnetizable materials, and can be targeted to particular locations in the body, or can be targeted for capture, containment, and removal. Also provided are bioresorbable nanoparticles prepared without the use of organic solvents, and methods for therapeutically using such bioresorbable nanoparticles.

35 Claims, 23 Drawing Sheets

(56) References Cited

U.S. PATENT DOCUMENTS

| | | | |
|---|---|---|---|
| 4,345,588 A | | 8/1982 | Widder et al. |
| 4,465,518 A | | 8/1984 | Miyoshi et al. |
| 4,501,726 A | | 2/1985 | Schroder et al. |
| 4,675,300 A | | 6/1987 | Zare et al. |
| 4,998,976 A | * | 3/1991 | Rapoport ............... 600/421 |
| 5,399,501 A | | 3/1995 | Pope et al. |
| 5,527,524 A | | 6/1996 | Tomalia et al. |
| 5,665,333 A | | 9/1997 | Homola et al. |
| 5,843,509 A | | 12/1998 | Calvo Salve et al. |
| 5,889,110 A | | 3/1999 | Hutchinson |
| 5,916,539 A | | 6/1999 | Pilgrimm |
| 5,921,244 A | * | 7/1999 | Chen et al. ............... 128/897 |
| 6,048,515 A | | 4/2000 | Kresse et al. |
| 6,200,547 B1 | * | 3/2001 | Volkonsky et al. .......... 424/9.36 |
| 6,576,221 B1 | | 6/2003 | Kresse et al. |
| 6,767,635 B1 | | 7/2004 | Bahr et al. |
| 7,081,489 B2 | | 7/2006 | Chen et al. |
| 7,175,909 B2 | | 2/2007 | Hu et al. |
| 7,175,912 B2 | | 2/2007 | Cui et al. |
| 7,218,962 B2 | | 5/2007 | Freyman |
| 7,249,604 B1 | | 7/2007 | Mohanraj |
| 7,833,544 B2 | | 11/2010 | Lewis et al. |
| 7,846,201 B2 | | 12/2010 | Chorny et al. |
| 8,097,283 B2 | | 1/2012 | Fisher et al. |
| 2001/0039450 A1 | * | 11/2001 | Pavcnik et al. ............. 623/1.24 |
| 2002/0103517 A1 | * | 8/2002 | West et al. ............... 607/88 |
| 2002/0133115 A1 | * | 9/2002 | Gordon et al. ............ 604/96.01 |
| 2002/0133225 A1 | | 9/2002 | Gordon |
| 2002/0151760 A1 | * | 10/2002 | Paturu ............... 600/15 |
| 2003/0044408 A1 | | 3/2003 | Levy et al. |
| 2003/0175492 A1 | | 9/2003 | Dames et al. |
| 2005/0014681 A1 | | 1/2005 | Minamitake et al. |
| 2005/0271745 A1 | | 12/2005 | Gruettner et al. |
| 2006/0002852 A1 | * | 1/2006 | Saltzman et al. ........... 424/1.11 |
| 2006/0041182 A1 | * | 2/2006 | Forbes et al. ............. 600/12 |
| 2006/0147413 A1 | | 7/2006 | Alferiev et al. |
| 2009/0216320 A1 | | 8/2009 | Levy et al. |
| 2011/0130616 A1 | | 6/2011 | Seeney et al. |

FOREIGN PATENT DOCUMENTS

| | | |
|---|---|---|
| WO | WO 2004/011861 | 2/2004 |
| WO | WO 2004/093643 | 11/2004 |
| WO | WO 2004093643 A2 * | 11/2004 |
| WO | WO 2005/110395 | 11/2005 |
| WO | WO 2005110395 A1 * | 11/2005 |
| WO | WO 2006/039675 | 4/2006 |

OTHER PUBLICATIONS

Joki et al. Continuous release of endostatin from microencapsulated engineered cells for tumor therapy. Nature Biotechnology. 19: 35-39, Jan. 2001.*

Extended European Search Report for Application No. EP 07 75 5754, Dated Aug. 3, 2010.

Plank et al., "The Magnetofection Method: Using Magnetic Force to Enhance Gene Delivery," May 2003, *Biol. Chem.*, vol. 384, pp. 737-747, Walter de Gruyter, Berlin, New York.

Kroetz et al., "Magnetofection—A Highly Efficient Tool for Antisense Oligonucleotide Delivery in Vitro and In Vivo", May 2003, *Molecular Therapy*, vol. 7, pp. 700-710, No. 5, The American Society of Gene Therapy.

Forrest et al., "A Degradable Polyethylenimine Derivative with Low Toxicity for Highly Efficient Gene Delivery," *Bioconjugate Chem.*, 2003, pp. 934-940, vol. 14, American Chemical Society.

Gosselin et al., "Efficient Gene Transfer Using Reversibly Cross-Linked Low Molecular Weight Polyethylenimine," *Bioconjugate Chem.*, 2001, pp. 989-994, vol. 12, American Chemical Society.

Arias et al., "Synthesis and Characterization of Poly(ethyl-2-cyanoacrylate) Nanoparticles with a Magnetic Core," Oct. 10, 2001, pp. 309-321, vol. 77, *Journal of Controlled Release*, Elsevier Science B.V.

Gomez-Lopera et al., "Synthesis and Characterization of Spherical Magnetite/Biodegradable Polymer Composite Particles," 2001, pp. 40-47, vol. 240, *Journal of Colloid and Interface Science*, Academic Press.

Igartua et al., "Development and Characterization of Solid Lipid Nanoparticles Loaded with Magnetite," 2002, pp. 149-157, vol. 233, *International Journal of Pharmaceutics*, Elsevier Science B.V.

Mueller et al., "Cytotoxicity of Magnetite-Loaded Polylactide, polylactide/Glycolide Particles and Solid Lipid Nanoparticles," 1996, pp. 85-94, vol. 138, *International Journal of Pharmaceutics*, Elsevier Science B.V.

Wagner et al., "Coupling of adenovirus to transferrin-polylysine/DNA complexes greatly enhances receptor-mediated gene delivery and expression of transfected genes," Jul. 1992, pp. 6099-6103, vol. 89, *Proc. Natl. Acad. Sci.*, USA.

Plank et al., "Magnetofection: Enhancing and Targeting Gene Delivery with Superparamagnetic Nanoparticles and Magnetic Fields," 2003, pp. 29-32, vol. 13, No. 1, *Journal of Liposome Research*, Marcel Dekker, Inc.

Scherer et al., "Magnetofection: enhancing and targeting gene delivery by magnetic force in vitro and in vivo", 2002, pp. 102-109, vol. 9, *Gene Therapy*, Nature Publishing Group.

Kroetz et al., "Magnetofection Potentiates Gene Delivery to Culture Endothelial Cells," *J Vasc Res*, 2003, pp. 425-434, vol. 40, S. Karger AG, Basel.

De Cuyper et al., "Magnetoliposomes Formation and Structural Characterizations," 1988, pp. 311-319, *European Biophysics Journal*, Springer-Verlag.

Khalafalla, "Magnetic Fluid," *Chemtech*, Sep. 1975, pp. 540-546.

Kumar, "Nano and Microparticles as Controlled Drug Delivery Devices," 2000, pp. 234-258, vol. 3, No. 2, *J Pharm Pharmaceut Sci.*

Quintanar-Guerrero et al., "Preparation Techniques and Mechanisms of Formation of Biodegradable Nanoparticles from Preformed Polymers," 1998, pp. 1113-1128, vol. 24, No. 12, *Drug Development of Industrial Pharmacy*.

Messai et al., "Elaboration of Poly(ethyleneimine) Coated Poly(D,L-lactic acid) Particles. Effect of Ionic Strength on the Surface Properties and DNA Binding Capabilities," 2003, pp. 293-305, vol. 32, *Colloids and Surfaces B: Biointerfaces*.

Hyeon, "Chemical Synthesis of Magnetic Nanoparticles," 2003, pp. 927-934, *The Royal Society of Chemistry*.

Sullivan et al., "Development of a Novel Gene Delivery Scaffold Utilizing Colloidal Gold-Polyethylenimine Conjugates for DNA Condensation," 2003, pp. 1882-1890, vol. 10, *Gene Therapy*.

Ito et al., "Magnetic Granules: a novel system for specific drug delivery to esophageal mucosa in oral administration," 1990, pp. 109-117, vol. 61, *International Journal of Pharmaceutics*.

Plank et al., "Enhancing and targeting nucleic acid delivery by magnetic force," 2003, pp. 745-758, vol. 3, No. 5, *Expert Opinion Biol. Ther.*

Forbes et al., "An Approach to Targeted Drug Delivery Based on Uniform Magnetic Fields," Sep. 2003, pp. 3372-3377, vol. 39, No. 5, *IEEE Transactions on Magnetics*.

Fricker, "Drug-eluting stents: flashy future or flash-in-the-pan?," Nov. 2001, pp. 1135-1137, vol. 6, No. 22, *Drug Discovery Today*.

Garas et al., "Overview of therapies for prevention of restenosis after coronary interventions," 2001, pp. 165-178, vol. 92, *Pharmacology & Therapeutics*.

Gershlick, "Treating atherosclerosis: local drug delivery from laboratory studies to clinical trials," 2002, pp. 259-271, vol. 160, *Atherosclerosis*.

Goodwin et al., "Targeting and retention of magnetic targeted carriers (MTCs) enhancing intra-arterial chemotherapy," 1999, pp. 132-139, vol. 194, *Journal of magnetism and Magnetic Materials*.

Hehrlein et al., "Drug-eluting stent: the "magic bullet" for prevention of restenosis?," 2002, pp. 417-423, vol. 97, No. 6, *Basic Research in Cardiology*.

Herr, PhD, "Presentation highlights: Prosthetic and orthotic limbs," May/Jun. 2002, pp. 11-12, vol. 39, No. 3, *Journal of Rehabilitation Research and Development*, VA/NIH Prosthetics Roundtable, http://www.vard.org/iour/02/39/3/suo/herr.htm.

(56) References Cited

OTHER PUBLICATIONS

Liu et al., "In-vitro investigation of blood embolization in cancer treatment using magnetorheological fluids," 2001, pp. 209-217, vol. 225, *Journal of Magnetism and Magnetic Materials*.

Regar et al., "Stent development and local drug delivery," 2001, pp. 227-248, vol. 59, *British Medical Bulletin*.

Schwartz et al., "Drug-Eluting Stents in Preclinical Studies: Recommended Evaluation From a Consensus Group," 2002, pp. 1867-1873, vol. 106, *Circulation: Journal of the American Heart Association*.

Segre et al., "Behaviour of macroscopic rigid spheres in Poiseuille flow," 1962, pp. 115-157, vol. 14, *Journal of Fluid Mechanics Digital Archive*.

Sheng et al., "In vitro investigation of a novel cancer therapeutic method using embolizing properties of magnetorheological fluids," 1999, pp. 167-175, vol. 194, *Journal of magnetism and Magnetic Materials*.

Berkowitz et al., "Influence of Cystallite Size on the Magnetic Properties of Acicular $\gamma$-$Fe_2O_3$ Particles*," *Journal of Applied Physics*, vol. 39, No. 2, Feb. 1, 1968, pp. 1261-1263.

Abe et al., "Enantioselective binding Sites on bovine serum albumin to dansyl amino acids," *Biochimica et Biophysica Acta* 1433 (1999) pp. 188-197.

Chorny et al., "Adenoviral Gene Vector Tethering to Nanoparticle Surfaces Results in Receptor-Independent Cell Entry and Increased Transgene Expression," *Molecular Therap*, vol. 14, No. 3, Sep. 2006, pp. 382-391.

International Search Report of PCT/US03/30431, dated Dec. 20, 2004.

International Search Report of PCT/US07/09603, dated Jan. 17, 2008.

Office Action dated Oct. 28, 2009, in U.S. Appl. No. 11/250,948.

* cited by examiner

UNIFORM FIELD MAGNETIZATION AND TARGETING OF THERAPEUTIC FORMULATIONS

CROSS REFERENCE TO RELATED APPLICATIONS

This application is a continuation-in-part of PCT application US2007/009603, filed Apr. 20, 2007, which claims priority to U.S. Application No. 60/794,191, filed Apr. 21, 2006. This application is also a continuation-in-part of U.S. application Ser. No. 11/250,948, filed Oct. 14, 2005 and issued as U.S. Pat. No. 7,846,201, which is a continuation-in-part of PCT application US2004/11861, filed Apr. 16, 2004, which claims priority to U.S. Application No. 60/546,233, filed Feb. 20, 2004. This application claims priority to U.S. Application No. 60/941,058, filed May 31, 2007. The disclosures of each of these applications are incorporated by reference herein, in their entirety and for all purposes.

STATEMENT OF GOVERNMENT SUPPORT

Research leading to the disclosed inventions was funded, in part, with funds from the National Institutes of Health, Grant No. HL72108, The National Heart Lung and Blood Institute, and the National Science Foundation, Grant No. 9984276. Accordingly, the United States Government may have certain rights in the invention.

FIELD OF INVENTION

This invention relates generally to the field of biotherapy. More specifically, the invention relates to the use of uniform magnetic fields to induce magnetization of magnetizable objects and generate magnetic field gradients. The resultant gradients can be used for magnetic targeting of magnetized or magnetizable nanoparticle therapeutic agents within the body of a subject.

BACKGROUND OF THE INVENTION

Various publications, including patents, published applications and scholarly articles, are cited throughout the specification. Each of these publications is incorporated by reference herein, in its entirety.

Therapeutic agents delivered in a conventional or non-specific manner often are distributed to non-designated areas of the body. As a consequence, the agent may be metabolized, for example, through first pass metabolism of the liver, thereby resulting in diminished bioavailability and the possibility for increased dosing at a higher cost and with the risk of adverse side effects. In addition, non-specific distribution of therapeutic agents may result in adverse effects and unwanted pharmacological responses in the subject to which they are administered. As a result, certain agents may be contraindicated in certain subjects or under certain conditions.

Implanting medical devices within a subject may necessitate follow-up chemotherapy, for example, to lessen the possibility for infection, to reduce inflammation, to repair tissue, or to prevent further local tissue damage. Drug-eluting devices, including stents, are increasingly used in a variety of biomedical applications to effectuate targeted delivery of drugs to the area of the implant. Drug-containing implants are limited, however, insofar as they generally contain only a small dose of a single therapeutic agent, and therefore lack the possibility for re-administration of the same or different therapeutic agent through the implanted device.

Nanoparticles and microparticles have shown potential as carrier systems for a variety of therapeutic agents, including enzymes for enzyme replacement therapy, hormones, cell modifying agents and genetic material as well as for imaging. Initial attempts to use nanoparticles and microparticles for site-specific delivery have shown potential to lower adverse effects in the patients to which they are administered, attributed in part to lower doses of therapeutic agents being required.

The foregoing discussion indicates that carrier systems show promise for optimizing agent administration, and as a possible vehicle for targeted drug delivery. Such technology is limited, however, in its capacity to actually effectuate optimized targeted delivery. In this regard, magnet targeting is considered an attractive way to achieve optimized targeted delivery of agents, particularly those formulated as a nanoparticle carrier. Preliminary attempts to deliver magnetized therapeutic agents or agent-containing magnetic carriers to specific locations in the body have shown promise, see U.S. Pat. No. 5,921,244. These methodologies, however, suffer from a major drawback, namely that this approach is restricted to targets that are close to the surface of the body.

Thus, a need exists for an optimized and efficacious targeting using magnetic carriers. It is desired that therapeutic systems allow for peripheral as well as local administration, and that the therapeutic system allow practioners to administer doses of agents that lessen untoward effects in patients, as well as allow administration of agents to patients in situations where they may otherwise be contraindicated due to the possibility of non-specific distribution or of high dose requirements. There is a further need to be able to remove unused or spent magnetic carriers to further lessen the possibility for untoward effects on the patient. The present invention addresses these and other long felt needs.

BRIEF SUMMARY OF THE INVENTION

The invention features systems for magnetically targeting therapeutic particles. Generally, the systems comprise a particle comprising at least one therapeutic agent and a first magnetic or magnetizable material, an implantable device such as a stent comprising a second magnetic or magnetizable material, and a retrieval system comprising a third magnetic or magnetizable material capable of being reversibly connected to a subject. In some aspect, the systems further comprise at least one magnetic field generator configured to generate a uniform magnetic field capable of magnetizing magnetizable material. The uniform magnetic field can generates at least one directable magnetic field gradient. The gradient can direct the particle to the device as well as direct any spent particles or particles that are not delivered to the device to the retrieval system. The magnetic field gradient can be generated proximal to the device and/or proximal to the retrieval system. The therapeutic agent can be any agent suitable to the therapeutic purpose to which it is being used, and can comprise a pharmaceutical, biomolecule, or cell, among other things. In some highly preferred aspects, the agent is a biomolecule such as a nucleic acid, and in particular a regulatory nucleic acid such as siRNA, shRNA, or miRNA. In some highly preferred aspects, the agent is a cell such as an endothelial cell, and in particular, a vascular endothelium cell.

The invention also features methods for magnetically targeting a therapeutic particle to an implanted device such as a stent. Generally, the methods can comprise administering to a subject a particle comprising at least one therapeutic agent and a first magnetic or magnetizable material, generating a uniform magnetic field capable of magnetizing magnetizable materials, and removing particles not delivered to the implanted device. In some aspects, the uniform magnetic field generates a magnetic field gradient proximal to the implanted device comprising a second magnetic or magnetizable material. In some aspects, the gradient targets the particle to the implanted device. The methods can further comprise removing spent particles. The therapeutic agent can be any agent suitable to the therapeutic purpose to which it is being used, and can comprise a pharmaceutical, biomolecule, or cell, among other things. In some highly preferred aspects, the agent is a biomolecule such as a nucleic acid, and in particular a regulatory nucleic acid such as siRNA, shRNA, or miRNA. In some highly preferred aspects, the agent is a cell such as an endothelial cell, and in particular, a vascular endothelium cell.

In some aspects of the inventive methods, removing particles not delivered to the implanted device comprises reversibly connecting a third magnetic or magnetizable material to the subject and generating a second magnetic field gradient proximal to the third magnetic or magnetizable material. The second magnetic field gradient can target the particles to the third magnetic or magnetizable material. It is highly preferred that the third magnetic or magnetizable material is reversibly connected to at least one blood vessel of the subject. In other aspects, removing particles not delivered to the implanted device can comprise removing the blood of the subject, contacting the blood with a third magnetic or magnetizable material, generating a second magnetic field gradient proximal to the third magnetic or magnetizable material, and returning the blood to the subject. The second magnetic field gradient can target particles to the third magnetic or magnetizable material. Preferably, the returned blood is substantially free of particles, and more preferably is free of particles.

In some aspects of the inventive methods, removing spent particles can comprise reversibly connecting a third magnetic or magnetizable material to the subject and generating a second magnetic field gradient proximal to the third magnetic or magnetizable material. The second magnetic field gradient targets the spent particles to the third magnetic or magnetizable material. In other aspects, removing spent particles can comprise removing the blood of the subject, contacting the blood with a third magnetic or magnetizable material, generating a second magnetic field gradient proximal to the third magnetic or magnetizable material, and returning the blood to the subject. The second magnetic field gradient targets the spent particles to the third magnetic or magnetizable material. Preferably, the returned blood is substantially free of the spent particles.

The invention also features methods for preparing nanoparticles. The methods can comprise providing a first aqueous solution comprising a water soluble salt of a mono-carboxylic fatty acid or a lipid mono-phosphate, a stabilizer such as albumin, and at least one therapeutic agent, and adding to the first aqueous solution a second aqueous solution comprising a polyvalent biocompatible cation such as calcium. The therapeutic agent can be taxol or all-trans retinoic acid. The water soluble salt of the fatty acid or the lipid mono-phosphate can be sodium oleate. The first aqueous solution can further comprise magnetic nanocrystals. The second aqueous solution can further comprise at least one cationic polypeptide such as poly-L-arginine. In some aspects, the methods further comprise forming the magnetic nanocrystals in the first aqueous solution.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1A:
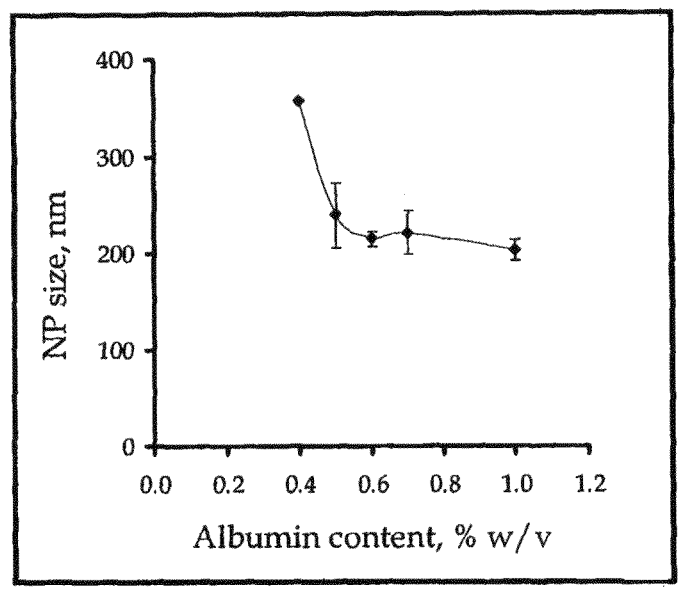
FIG. 1A shows the relationship between the size of nanoparticles (NP) and the concentration of stabilizer. 1B shows the relationship between the yield of nanoparticles (NP) and the concentration of stabilizer.

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

As used in this specification and the appended claims, the singular forms "a," "an," and "the" include plural referents unless the content clearly dictates otherwise. Thus, for example, reference to "a particle" includes a combination of two or more particles, and the like.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Polynucleotide," also referred to as "nucleic acid" or "nucleic acid molecule," refers to any polyribonucleotide or polydeoxyribonucleotide, which may be unmodified RNA or DNA or modified RNA or DNA. Polynucleotides include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons. Modified bases include, for example, tritylated bases and unusual bases such as inosine. A variety of modifications can be made to DNA and RNA; thus, polynucleotide embraces chemically, enzymatically or metabolically modified forms of polynucleotides as typically found in nature, as well as the chemical forms of DNA and RNA characteristic of viruses and cells. Polynucleotide also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. Polypeptide refers to both short chains, commonly referred to as peptides, oligopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications.

Except when noted, "subject" or "patient" are used interchangeably and refer to any animal, but preferably refer to mammals such as humans and non-human primates, as well as companion, farm, or experimental animals such as rabbits, dogs, cats, rats, mice, horses, cows, pigs, and the like. Humans are most preferred.

"Effective amount" or "therapeutically effective amount" are used interchangeably herein, and refer to an amount of a therapeutic agent, as described herein, effective to achieve a particular biological result such as, but not limited to, biological results disclosed, described, or exemplified herein, as determined by any means suitable in the art.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the therapeutic agent(s) and is not toxic to the host to which it is administered.

It has been discovered in accordance with the present invention that therapeutic agents can be targeted to specific locations in the body through use of uniform magnetic fields to induce magnetization of magnetizable objects and to generate a magnetic field gradient. It has further been discovered that magnetic targeting can be utilized for any type of therapeutic agent, including pharmaceutical or chemical compounds, biomolecules, and cells. Accordingly, the invention features systems and methods for magnetically targeting therapeutic agents to one or more desired locations in the body.

In one aspect, the systems comprise therapeutic agents provided as part of a therapeutic formulation. The therapeutic formulation can comprise an effective amount of a therapeutic agent and a particle, which particle can comprise a magnetic or magnetizable material. Preferably, the particle is a nanoparticle. The associated particle and therapeutic agent are synonymously referred to herein as a therapeutic particle. Magnetic nanoparticles include particles that are permanently magnetic and those that are magnetizable upon exposure to an external magnetic field, but lose their magnetization when the field is removed. Materials that are magnetic or magnetizable upon exposure to a magnetic field that lose their magnetic properties when the field is removed are referred to herein as superparamagnetic material. Superparamagnetic particles are preferred to prevent irreversible aggregation of the particles. Examples of suitable superparamagnetic materials include, but are not limited to, iron, mixed iron oxide (magnetite), or gamma ferric oxide (maghemite) as well as substituted magnetites that include additional elements such as zinc. Preferably, the superparamagnetic material is in the form of one or more nanocrystals, for example, single-domain crystalline systems with at least one dimension ≤100 nm. A nanocrystal is any nanomaterial with at least one dimension ≤100 nm and that is singlecrystalline or monocrystalline, formed of a single crustal-unit, and so all elements have identical crystallographic orientation of c- and a-axes and overgrow as one unit. Any particle that exhibits regions of crystalinity can be termed nanoparticle or nanocluster based on dimensions.

Ferromagnetic crystals can be comprised of magnetized domains the size of a micron. Superparamagnetism can occur when the size of the crystals is smaller than the ferromagnetic domain (~30 nm), see http://www.ncbi.nlm.nih.gov/books/bv.fcgi?rid=micad.chapter.USPIO=CD20MAb. Superparamagetic properties can depend on temperature. Temperature can, under some conditions, destabilize the magnetism. Without intending to be limited to any particular theory or mechanism of action, it is believed that thermal energy may prevent the alignment of the magnetic moments present in superparamagnetic materials. After the removal of an applied magnetic field, the magnetic moments of superparamagnetic materials still exist, but are in rapid motion, causing a randomly oriented or disordered magnetic moment and, thus, no net magnetic field. At the temperatures of biological systems and int eh applied magnetic fields of MR imagers, superparamagnetic materials are less magnetic than their ferromagnetic counterparts. For example, it has been noted that magnetism of small superparamagnetic iron oxides decreases at elevated temperatures. (Berkowitz et al. (1968) J. Appl. Phys. 39:1261).

The superparamagnetic nanocrystals can range in size from about 1 nm to about 20 nm, depending on, among other things, the preparation method and medium composition. Preferably, the nanocrystals are smaller than 10-20 nm to ensure superparamagnetic properties of the material. More preferably, the nanocrystals are from about 5 nm to about 20 nm.

In some aspects, the particle is a composite nanocrystal. The composite nanocrystal can comprise more than one individual magnetic or magnetizable nanocrystals and one or more water-insoluble biocompatible materials to hold the crystals together. The biocompatible materials can be a polymer, which can be biodegradable or non-biodegradable. Non-limiting examples of such polymers include poly(urethane), poly(ester), poly(lactic acid), poly(glycolic acid), poly(lactide-co-glycolide), poly(ε-caprolactone), poly(ethyleneimine), poly(styrene), poly(amide), rubber, silicone rubber, poly(acrylonitrile), poly(acrylate), poly(metacrylate), poly(α-hydroxy acid), poly(dioxanone), poly(orthoester), poly(ether-ester), poly(lactone), poly(alkylcyanoacrylate), poly(anhydride), poly(ethylenvinyl acetate), poly(hydroxybutyrate), poly(tetrafluoroethylene), poly(ethylene terephthalate, polyoxyethylene, polyoxyethlkyene-polyoxypropylene block copolymers, mixtures thereof and copolymers of corresponding monomers.

Polymeric nanoparticles with incorporated superparamagnetic nanocrystals can be prepared according to any means suitable in the art. For example, the nanoparticles can be prepared by dispersing the superparamagnetic nanocrystals in an organic solvent, in which the polymer and/or the therapeutic agent is dissolved, emulsifying the organic phase in water in the presence of a suitable stabilizer, and finally eliminating the solvent to obtain solidified nanoparticles. Conditions of nanoparticle preparation should not be damaging for the therapeutic agent to be attached. The temperature for nanoparticle preparation preferably ranges from about 25° C. to about 37° C., although higher or lower temperatures can be used. Non-limiting examples of ways to prepare superparamagnetic nanoparticles for biological applications are described in U.S. Pat. Nos. 7,175,912 and 7,175,909, and U.S. Publication No. 20050271745. Magnetic nanoparticles, information for the development of magnetic nanoparticles, and reagents for the preparation of magnetic nanoparticles (MNP) are commercially available.

The particles can be composed of the salts/complexes of anionic lipids, for example, fatty acids or lipid phosphates with polyvalent biocompatible cations. The particles can be formed under mild conditions through combination of the respective aqueous solutions in the presence of colloid stabilizers, thus avoiding use of organic solvents and without need for external mechanical energy input.

In some preferred aspects, the particles are bioresorbable nanoparticles, including those prepared without the use of high energy dispersion or organic solvents. Bioresorbable nanoparticles can be comprised of at least one anionic lipid salt, at least one therapeutic agents, and at least one magnetic or magnetizable material.

To prepare bioresorbable nanoparticles, a first aqueous solution is provided. The first aqueous solution comprises i) a water soluble salt of a mono-carboxylic fatty acid or a lipid phosphate/phosphanate, ii) a stabilizer, and iii) a therapeutic agent. Exemplary soluble salts include, but are not limited to, the lithium, sodium, ammonium, and potassium salts. An aqueous solution of the fatty acid salt can be prepared, for example, by adding the fatty acid and base, such as sodium hydroxide, to water and dissolving the fatty acid.

Fatty acids that can be used include straight and branched chain, saturated and unsaturated mono-carboxylic fatty acids having eight or more carbon atoms, particularly eight to thirty carbon atoms. Typical mono-carboxylic fatty acids include caprylic acid (octanoic acid), 2-ethyl octanoic acid, capric acid (decanoic acid), 2-ethyl-decanoic acid, 11-undecenoic acid, undecanoic acid, 2-ethyl-dodecanoic acid, cis-5-dodecenoic acid, lauroleic acid (cis-9-dodecanoic acid), traumatic acid (2-dodecenoic acid), lauric acid (dodecanoic acid), brassylic acid (tridecanoic acid), 2-ethyl-tetradecanoic acid, myristoleic acid (cis-9-tetradecanoic acid), tsuzuic acid (cis-4-tetradecenoic acid), myristic acid (tetradecanoic acid), pentadecanoic acid, 2-ethyl-hexadecanoic acid, palmitoleic acid (cis-9-hexadecanoic acid), palmitic acid (hexadecanoic acid), heptadecanoic acid, margaric acid (heptadecanoic acid), petroselic acid (cis-6-octadecenoic acid), 2-ethyl-octadecanoic acid, oleic acid (cis-9-octadecenoic acid), elaidic (trans-9-octadecenoic acid), asclepinic acid (cis-11-octadecenoic acid), vaccenic acid (trans-11-octadecenoic acid), taxoleic acid (cis, cis-5,9-octadecadienoic), linoleic acid (cis, cis-9,12-octadecadienoic acid), linolenic acid (cis, cis, cis-9,12,15-octadecatrienoic acid), stearic acid (octadecanoic acid), tuberculostearic acid (10-methyl octadecanoic acid), nonadecanoic acid, 2-ethyl-eicosanoic acid, arachidonic acid (5,8,11,14-eicosatetraenoic acid), cis-8,11,14-eicosatrienoic acid, gadoleic acid (cis-9-eicosenoic acid), gondoic acid (cis-11-eicosenoic acid), arachidic acid (eicosanoic acid), 2-ocyl-dodecanoic acid, erucic acid (cis-13-docosenoic acid), behenic acid (docosanoic acid), tricosanoic acid, selacholeic acid (cis-15-tetracosanoic acid), lignoceric acid (tetracosanoic acid), ximenic acid (cis-17-hexacosenoic acid), and hexacosanoic acid. A particularly preferred fatty acid is oleic acid.

Hydroxy acids such as 11-hydroxy-undecanoic acid, ricinoleic acid (12-hydroxy-cis-9-octadecenoic acid), lesquerolic acid (14-hydroxy-cis-11-eicosenoic acid: 20:1-OH), densipolic acid (12-hydroxy-cis, cis-9,15-octadecadienoic acid) auricolic acid (14-hydroxy-cis, cis-11,17-eicosadienoic acid), 9,10-dihydroxyoctadecanoic acid, 9,14-dihydroxyoctadecanoic acid, and phellonic acid (22-hydroxydocosanoic acid) can also be used.

Lipid phosphates, such as the water soluble mono-phosphate salts of alcohols having eight or more carbon atoms, more preferably eight to thirty carbon atoms, can also be used. Such phosphates include α-tocopherol phosphate disodium salt, oleyl phosphate disodium salt, and the disodium salts of the phosphate esters of straight and branched chain, saturated and unsaturated mono-alcohols having eight or more carbon atoms, such as the disodium salts of the phosphate esters of n-decanol, n-dodecanol, n-tetradecanol, n-hexadecanol, and n-octadecanol.

A colloidal stabilizer, or mixture of colloid stabilizers, can be added to the aqueous solution of the fatty acid salt or to the aqueous solution containing the polycation. Colloidal stabilizers are materials believed to be adsorbed onto the nanoparticles, thereby providing charge or steric protection of the particles from aggregation. Suitable stabilizers include secondary colloids, such as gelatin, agar-agar, starch, cellulose derivatives such as carboxymethyl cellulose and hydroxypropyl cellulose, and proteins, such as albumin. Non-ionic surfactants, such as polyethylene oxide, ethylene oxide/propylene oxide block co-polymers, for example, PLURONIC® surfactants, and ethoxylated fatty acid esters of esters of sorbitol, such as polyoxyethylene (20) sorbitan monolautate (TWEEN® 20), polyoxyethylene (20) sorbitan monopalmitate (TWEEN® 40), polyoxyethylene (20) sorbitan monosterate (TWEEN® 60), polyoxyethylene (20) sorbitan monooleate (TWEEN® 80), or polyoxyethylene (20) sorbitan trioleate (TWEEN® 85) can also be used. A preferred stabilizer is albumin.

A second aqueous solution comprising a water-soluble salt of a polyvalent biocompatible metal or organic cation can be added to the first aqueous solution. A cation is biocompatible if it is non-toxic to the recipient in the quantities used, and also presents no significant deleterious or untoward effects on the recipient's body. Useful biocompatible polyvalent cations include, without limitation, $Al^{+3}$, $Ca^{+2}$, $Mg^{+2}$, $Zn^{+2}$, $Ba^{+2}$, $Sr^{+2}$, $Fe^{+2}$, and $Cu^{+2}$, polyarginine, protamine. A preferred biocompatible polyvalent cation is $Ca^{+2}$.

The size of the bioresorbable particles can be readily controlled and adapted for specific applications by adjusting the amount of the stabilizer, lipid salt, and polyvalent biocompatible cation. Although the particles are generally lipophilic, showing high affinity for hydrophobic therapeutic agents, ionic water-soluble therapeutic agents can also be encapsulated as their water-insoluble salts/complexes in the process of particle formation. The nature and amount of the lipid salt and polyvalent biocompatible cation can be varied in order to adjust the relative lipophilicity of the resulting particles.

A cationic peptide, cationic protein, or a mixture of cationic peptides and/or cationic proteins can also be co-added to the second aqueous solution containing a metal polycation. Preferred cationic peptides contain at least about 50%, preferably at least about 70%, and more preferably at least about 85% of basic amino acid residues, such as arginine, lysine, and guanidine, and contain more then five amino acid residues, preferably about 10 to about 1000 residues. More preferred cationic peptides include arginine-rich polypeptides, such as poly-L-arginine. More preferred peptides are arginine-rich proteins, such as protamine. Guanidinium-rich proteins can also be used. Synthetic organic polycations-(polypeptide-like substances), such as polyethyleneimine, can also be used.

Bioresorbable nanoparticles can be rendered magnetic through inclusion of magnetically responsive nanocrystals in their structure, for example, by combining a fine suspension of such crystals (a ferrofluid) with the anionic lipid solution prior to the particle formation. Ferrofluids are composed of nanosacle ferromagnetic particles suspended in a carrier fluid, such as water. Preparation of such nanoparticles is a two-step process consisting of 1) making the fine suspension of magnetic nanocrystals (ferrofluid) in the presence of an anionic lipid, and 2) forming nanoparticles by controlled precipitation of the anionic lipid with a polyvalent cation in the presence of a stabilizer and a therapeutic agent. In one aspect, the magnetic nanoparticles are prepared by controlled aggregation of an oleate-stabilized ferrofluid with $Ca^{+2}$.

To prepare a ferrofluid, an aqueous solution containing a water soluble ferric ($Fe^{+3}$) salt, such as ferric chloride hexahydrate, and a water soluble ferrous salt ($Fe^{+2}$), such as ferrous chloride tetrahydrate, is precipitated with base, such as an aqueous sodium hydroxide solution to form a magnetite precipitate containing magnetic nanocrystals. A water soluble salt of a fatty acid, such as an aqueous solution of sodium oleate, is added, and the magnetic nanocrystals resuspended by heating, for example, in an inert atmosphere, such as under argon. A stabilizer such as albumin can be added, along with the therapeutic agent, either to the first aqueous solution, which comprises the magnetic nanocrystals, stabilizer, water soluble salt of a mono-carboxylic fatty acid, and therapeutic agent, or to the second aqueous solution, which comprises the polyvalent biocompatible cation. The second solution is then added to form the magnetic nanoparticles.

In some aspects, the therapeutic agent can be attached or tethered to the surface of a pre-formed nanoparticle. The attachment can be according to any means suitable for the therapeutic application to which the agent will be used, or according to the chemical properties of the agent or the nanoparticle. For example, attachment can be by adsorption, electrostatic interactions, charge complexation, or covalent binding, including the use of biomolecule tethers. Non-limiting examples of procedures for associating therapeutic agents with nanoparticles are described in U.S. Pat. Nos. 7,081,489, 6,048,515, 6,576,221, and 6,767,635.

The magnetic nanoparticles associated with the therapeutic agent can range in size from about 50 to about 500 nm. The size can vary according to any appropriate variable. Preferably, the nanoparticles range in size from about 50 nm to about 200 nm, and more preferably from about 100 nm to about 200 nm.

The particle can be derivatized, and the surface of the particle can be modified to facilitate derivatization. For example, the particles can be coated with a thiol-reactive and photoactivatable polymer. Irradiation can facilitate the covalent binding of the polymer to the surface, and its thiol-reactive groups can subsequently be used to attach agents providing stealth properties in the blood circulation and/or specific binding to a target tissue. Photochemical activation of surfaces for attaching biomaterial is described in US Publ. No. 20060147413.

Extended circulation time of particles associated with a therapeutic agent can be achieved by preventing opsonization and clearance by the subject's immune system by coating the particle with a biocompatible hydrophilic polymer such as polyethyleneglycol or dextran, or by coating the particle with albumin to inhibit the binding of opsonins to the particle surface.

Preparation of Modified Particles can Proceed According to any Means Suitable in the art. For example, a magnetically responsive agent, iron oxide, can be produced. Fine dispersion of iron oxide in a suitable organic solvent is typically obtained as follows: an aqueous solution containing ferric and ferrous chlorides is mixed with an aqueous solution of sodium hydroxide. The precipitate is coated with oleic acid by short incubation at 90° C. in ethanol. The precipitate is washed once with ethanol to remove free acid and dispersed in chloroform.

The resulting organic dispersion of iron oxide in chloroform is used to dissolve a biodegradable polymer, polylactic acid (PLA) or its polyethyleneglycol conjugate (PLA-PEG), thus forming an organic phase. The organic phase is emulsified in an aqueous albumin solution (1%) by sonication on an ice bath followed by evaporation of the organic solvent. The particles are separated from the unbound albumin by repeated magnetic sedimentation/resuspension cycles.

In an alternative aspect, a post-formation surface modification can be used. For example, particles can be formed using a photoreactive polymer (e.g., PBPC/PBMC (polyallylamine-benzophenone-pyridyldithio/maleimido-carboxylate polymer) as a stabilizer in the aqueous phase. Subsequent brief ultraviolet irradiation achieves covalent binding of the polymer to the magnetic nanoparticle. The resulting particles are reacted in suspension with a thiolated polyethyleneglycol, which allows better control over the particle size and the extent of surface modification.

Therapeutic agents include any molecules that can be associated with a particle and used in the systems and methods of the present invention. Agents can be purified molecules, substantially purified molecules, molecules that are one or more components of a mixture of compounds, or a mixture of a compound with any other material. Agents can be organic or inorganic chemicals, radioisotopes, pharmaceutical compounds, pharmaceutical salts, pro-drugs, or biomolecules, and all fragments, analogs, homologs, conjugates, and derivatives thereof. Biomolecules include, without limitation, proteins, polypeptides, nucleic acids, lipids, polysaccharides, monosaccharides, and all fragments, analogs, homologs, conjugates, and derivatives thereof. Agents can also be an isolated product of unknown structure, a mixture of several known products, or an undefined composition comprising one or more compounds. Examples of undefined compositions include cell and tissue extracts, growth medium in which prokaryotic, eukaryotic, and archaebacterial cells have been cultured, fermentation broths, protein expression libraries, and the like. Agents can also be one or more cells, including eukaryotic or prokaryotic cells, or can be one or more viruses. Therapeutic agents can be provided in or otherwise associated with a carrier such as a pharmaceutically acceptable carrier.

Therapeutic agent also includes viral vector systems, which are used in gene therapy. A number of viral vector systems under development, such as adenovirus, adeno-associated virus, retrovirus and *Herpes simplex* virus. One of the most successful ways of introducing the gene of interest into the appropriate cell line uses recombinant adenovirus. Adenoviruses are non-enveloped particles having a diameter of about 70 nm, and contain a linear double stranded DNA of approximately 36,000 base pairs. They are easily prepared with high titers and can infect a wide range of cells, including non-dividing cells. Recombinant adenovirus can also be used in vaccination by expressing a gene product that triggers an immune response.

Adeno-associated viruses have a particle diameter of 20 nm. Retroviruses are spherical, enveloped particles having a particle diameter of between about 80 nm to about 100 nm in diameter. Retroviruses have been widely used as vectors for DNA delivery. *Herpes simplex* viruses have a particle diameter of about 100 nm, and contain enveloped, double-stranded DNA virus of approximately 150,000 base pairs. These viruses have a large loading capacity for foreign genes and are able to infect a wide range of cells. In addition, the virus genome remains episomal after infection, thus eliminating the possibility of opportunistic malignant insertional mutagenesis of the host genome. *Herpes viruses* have been exploited for specific gene transfer trials into the central nervous system.

Multiple agents can be included in a particle. Those of skill in the art can determine the particular combination of agents, based, for example, on the condition being treated, or on the needs of the particular subject. For example, additional agents that modulate the activity of a primary agent, reduce pain, support growth of therapeutic cells, are antithrombogenic, anti-apoptotic, anti-inflammatory, immunosuppressants, or antioxidants, or other agents ordinarily used in the art to treat the disease of interest can be used.

The therapeutic agents can also be formulated in sustained release vehicles or depot preparations. For example, the agents can be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well-known examples suitable for use as carriers for hydrophobic drugs.

In some preferred aspects, the therapeutic agents are regulatory nucleic acids. For example, regulatory nucleic acids can be used to facilitate post-transcriptional gene silencing (RNA silencing). RNA silencing involves the processing of double-stranded RNA (dsRNA) into small 21-28 nucleotide fragments by an RNase H-based enzyme. The cleavage products are siRNA (small interfering RNA) or miRNA (microRNA), which regulate gene expression in a sequence-specific manner. Regulatory nucleic acids can be part of a plasmid or other suitable vector, for example, administered as DNA that is transcribed and processed to regulatory RNA.

siRNAs may thus comprise RNA molecules having a double-stranded region approximately 19 nucleotides in length with 1-2 nucleotide 3' overhangs on each strand, resulting in a total length of between approximately 21 and 23 nucleotides. As used herein, siRNAs also include various RNA structures that may be processed in vivo to generate such molecules. Such structures include RNA strands containing two complementary elements that hybridize to one another to form a stem, a loop, and optionally an overhang, preferably a 3' overhang. Preferably, the stem is approximately 19 bp long, the loop is about 1-20, more preferably about 4-10, and most preferably about 6-8 nt long and/or the overhang is about 1-20, and more preferably about 2-15 nt long. In certain embodiments of the invention the stem is minimally 19 nucleotides in length and may be up to approximately 29 nucleotides in length. Loops of 4 nucleotides or greater are less likely subject to steric constraints than are shorter loops and therefore may be preferred. The overhang may include a 5' phosphate and a 3' hydroxyl. The overhang may, but need not comprise a plurality of U residues, e.g., between 1 and 5 U residues.

miRNAs are typically between approximately 20 and 26 nucleotides in length, e.g., 22 nt in length. It is believed that they are derived from larger precursors known as small temporal RNAs (stRNAs) or mRNA precursors, which are typically approximately 70 nt long with an approximately 4-15 nt loop.

Viral vectors or DNA vectors encoding short hairpin RNA (shRNA) which are processed in the cell cytoplasm to short interfering RNA (siRNA) can also be used. A plasmid containing a DNA sequence encoding for a particular desired siRNA sequence can be delivered to a target cell, and subsequently internalized, for example, by virally-mediated infection. Once in the cell, the DNA sequence is continuously transcribed into RNA molecules that loop back on themselves and form hairpin structures through intramolecular base pairing. These hairpin structures, once processed by the cell, are equivalent to transfected siRNA molecules and are used by the cell to mediate RNAi of the desired protein. The use of shRNA has an advantage over siRNA as the former can lead to stable, long-term inhibition of protein expression. In cases where longer periods of protein inhibition are necessary, shRNA as the therapeutic agent is preferable.

In some preferred aspects, the therapeutic agent is one or more cells. For example, the cell can be a stem cell such as a postpartum derived cell or bone marrow derived cell or can be a progenitor cell, Blood Outgrowth Endothelial Cell (BOED), adult and cord blood stem cells (CBSC), Induced Pluripotent Stem Cells, e.g., skin cells that are programmed to transform into pluripotent stem cells with further potential to differentiate them into cell with at least one endothelial phenotype. In some exemplary aspects, the cell is a vascular cell such as a vascular endothelial cell. Endothelial cells can be autologous, heterologous, or derived from either blood, bone marrow, or tissue biopsy. Tissue biopsied endothelial cells can be derived from arteries, veins, adipose tissue, or any other tissue with the potential to contain endothelial cells or their progenitors.

In some aspects, the systems comprise an implantable device. Any implantable device known or used in the art can be utilized in the inventive systems. Non-limiting examples of suitable implantable device include stents, heart valves, wire sutures, temporary joint replacements and urinary dilators, orthopedic implants such as joint prostheses, screws, staples, nails, nuts, bolts, plates, rods, pins, wires, inserters, osteoports, halo systems and other orthopedic devices used for stabilization or fixation of spinal and long bone fractures or disarticulations. Other devices include non-orthopedic devices, temporary placements and permanent implants, such as traceostomy devices, drainage ducts, jejunostomy and gastrostomy tubes, intraurethral and other genitourinary implants, stylets, dilators, vascular clips and filters, pacemakers, wire guides and access ports of subcutaneously implanted vascular catheters, electronic chips, transmitting/receiving micro-electronic implants, implantable drug delivery microdevices, implantable biosensors, implantable micro-video devices, and implantable microbattery devices. A highly preferred implantable device is a stent. The stent can be a drug-eluting stent.

Preferably, the implantable device comprises a magnetic or magnetizable material. More preferably, such magnetic or magnetizable materials are biocompatible. The device can be modified to be biocompatible. For example, surface modifications of metal supports to improve biocompatibility are described in US Publ. No. 20030044408.

Stainless steel, for example, Grade 304 Stainless Steel is one preferred non-limiting example of a material that can be used in the implantable device. Other examples includes the 200-series austenitic chromium-nickel-manganese alloys and 300-series austenitic chromium-nickel alloys.

The device can be implanted anywhere in the body of the subject. In some preferred aspects, the device is implanted in the vascular system of the subject, for example, in a blood vessel such as a vein, artery, or capillary. Where stents are used, the stents can be implanted in any duct such as a hepatic duct, bile duct, parts of the digestive system such as the esophagus, stomach, intestines, or colon, parts of the respiratory system such as the trachea or bronchi, or parts of the excretory system such as the ureter, urethra, or renal excretory duct. Other implants include ocular implants and radioactive seeds.

In some aspects, the systems can comprise a retrieval system. In general, the retrieval system can be used to capture and contain therapeutic particles that do not reach the target site, or to capture and contain particles after the therapeutic agent has been delivered to the target site, synonymously referred to herein as spent particles. Unused or spent particles may enter or remain in the blood of the subject, and may produce untoward effects in the subject. To minimize risks to the subject, it is preferable to remove such unused and/or spent particles. The retrieval system preferably capture and contains most, and more preferably substantially all unused and/or spent particles such that the body or particular fluid, organ, appendage, and the like within the body is substantially free of spent or unused particles.

In some preferred aspects, the retrieval system comprises a magnetic or magnetizable material. The material can be provided in any form suitable in the art. For example, the material can be a rod, plate, bead, tube, wire, panel, filter, screen, mesh, and the like. The particular form (geometry) is not critical, and can vary according to any number of variables.

The retrieval system is preferably biocompatible. Suitable materials that can be used to comprise the retrieval system include, but are not limited to stainless steel such as 316L stainless steel. 400-series stainless steel, including 430-grade can also be used in some instances, such as those for short term use where potential long-term corrosive properties of retrieval system materials is not of concern.

Preferably, the retrieval system is configured such that it is capable of being reversibly connected to the subject. The retrieval system can be reversibly connected to a subject at any location on the body suitable according to the therapeutic use to which the overall system is being used. For example, the retrieval system can be reversibly connected to the body surface, or to a particular interior organ, bone, or system. Preferably, the retrieval system is reversibly connected to at least one blood vessel, and more preferably to the lumen of the blood vessel to allow blood to directly flow into the retrieval system. The circulatory system is a high-flow, well-accessed system, and is thus highly preferred for connection to a retrieval system.

In some aspects, the retrieval system is indirectly connected to the subject. For example, a biological fluid of the subject can be removed and contacted with the retrieval system. Biological fluids can include, but are not limited to blood, cerebrospinal fluid, ascites fluid, bile, amniotic fluid, milk, saliva, gingival crevicular fluid, urine, mucosal fluid, renal fluid, and the like. After the particles are sequestered from the biological fluid, the biological fluid can be returned to the subject. Blood is a particularly preferred biological fluid. Thus, for example, the subject's blood may be removed from the body, contacted with the retrieval system, and returned to the body by transfusion. The blood can be separated into its components or can remain as whole blood.

Particles directed to the retrieval system can be disposed of according to any means suitable in the art. After the particles are directed to the retrieval system, the retrieval system can be removed from the subject.

The particles comprising at least one therapeutic agent and at least one magnetic or magnetizable material are targeted to one or more desired locations in the body, for example, to one or more implanted devices in the body, through a magnetic field. Thus, the inventive systems can comprise a magnetic field generator. The magnetic field generator can include an external magnet, including a magnetic resonance imaging device. In some aspects, the magnetic field generator is configured to generate at least one directable magnetic field gradient. The magnetic field gradient can direct the particle to the implantable device. The magnetic field gradient can direct particles not delivered to the device to the retrieval system, or can direct spent particles, that is, particles that have successfully delivered and are depleted of the therapeutic agent to the retrieval system. A single magnetic field gradient can be used to direct the particles to the implantable device, and then reconfigured to direct extant unused or spent particles to the retrieval system. Alternatively, multiple gradients can be produced and used, with at least one gradient directing particles to the implanted device, and at least one additional gradient directing particles to the retrieval system. The gradient can be generated proximal to the implanted device, and can be generated proximal to the retrieval system.

Figure 4:
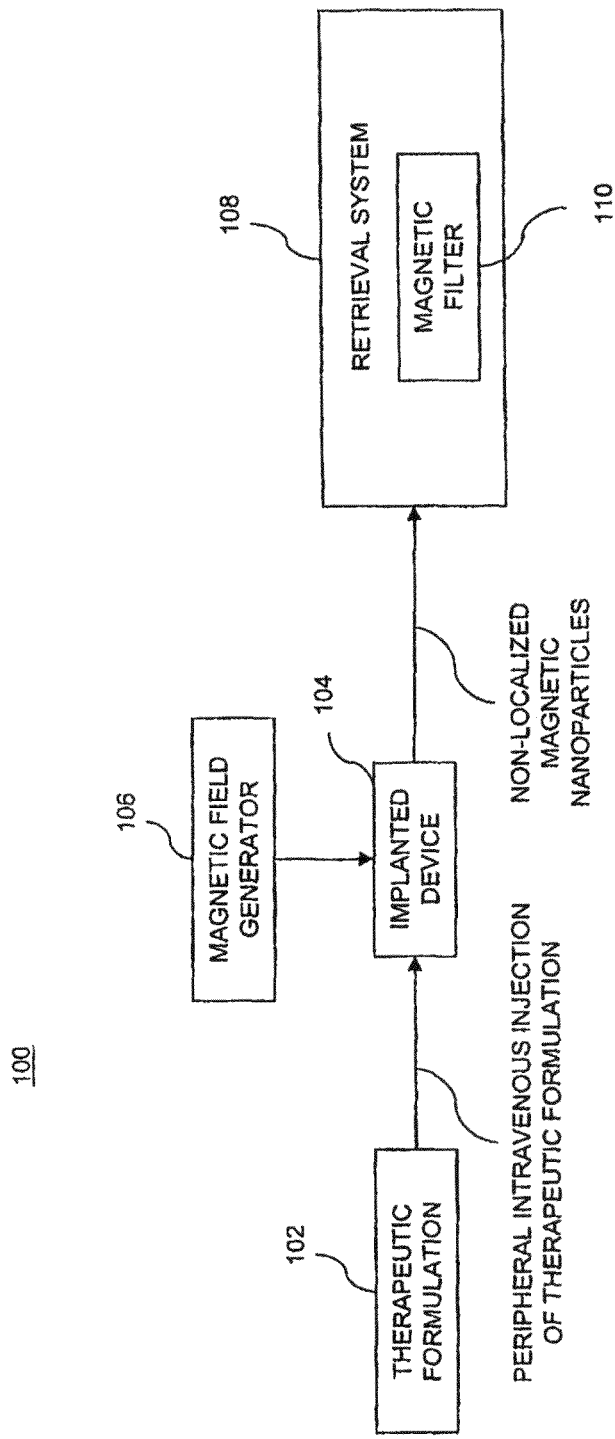
FIG. 4 shows an exemplary magnetically assisted therapeutic system according to an embodiment of the invention.
Figure 5:
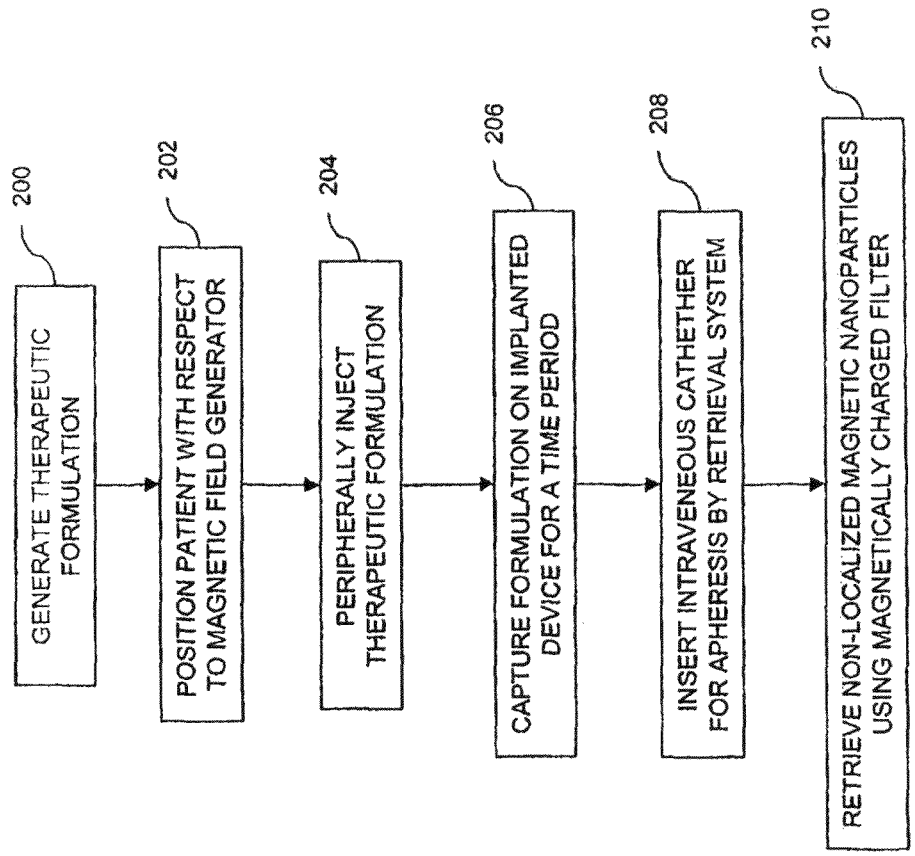
FIG. 5 shows a flowchart illustrating an exemplary method for administering a therapeutic agent to an implanted device and for retrieving magnetic carrier nanoparticles that do not localize on the implanted device, according to an embodiment of the invention.

Referring to FIGS. 4 and 5, an exemplary magnetically assisted therapeutic system 100 is illustrated. The therapeutic system 100 comprises a device 104 that has been implanted in a mammalian subject (not shown), a magnetic field generator 106, configured to generate a magnetic field gradient external to the subject that is directed proximally to the implanted device 104, and a therapeutic particle 102 that has been administered to the subject. Device 104 can be a vascular device that has been implanted in the vascular system of the mammalian subject.

Also featured in accordance with the present invention are methods for magnetically targeting a therapeutic particle to one or more desired locations in or on a subject. In one preferred aspect, the methods are applicable to magnetically target a therapeutic particle to a device implanted in a subject.

The methods can comprise administering to a subject having an implanted device comprising at least one biocompatible magnetic or magnetizable material a therapeutic particle comprising at least one therapeutic agent and at least one magnetic or magnetizable material, generating a magnetic field gradient proximal to the implanted device, wherein the gradient targets the particle to the implantable device, and removing particles not delivered to the implantable device, or removing spent particles.

The therapeutic agent can be any molecule as described or exemplified herein, including without limitation, a pharmaceutical, biomolecule, or cell. The implanted device can be any device used, known, or otherwise suitable in the art such as those described or exemplified herein.

Administration of the therapeutic particles can be by infusion or injection (intravenously, intramuscularly, intracutaneously, subcutaneously, intrathecal, intraduodenally, intraperitoneally, and the like). The particles can also be administered intranasally, vaginally, rectally, buccally, orally, or transdermally. Preferably, the compositions are administered intravenously. Administration can be at the direction of a physician. The particles can be administered proximally or distally to the implanted device.

For buccal administration, the compositions may take the form of tablets, troche or lozenge formulated in conventional manner. Compositions for oral or buccal administration, may be formulated to give controlled release of the particles. Such formulations may include one or more sustained-release agents known in the art, such as glyceryl mono-stearate, glyceryl distearate and wax.

Particles may be applied topically. Such administrations include applying the particles externally to the epidermis, the mouth cavity, eye, ear and nose. Particles for use in topical administration include, e.g., liquid or gel preparations suitable for penetration through the skin such as creams, liniments, lotions, ointments or pastes, and drops suitable for delivery to the eye, ear or nose.

Various alternative pharmaceutical delivery systems may be employed. Non-limiting examples of such systems include liposomes and emulsions. Certain organic solvents such as dimethylsulfoxide also may be employed. Additionally, the particles may be delivered using a sustained-release system, such as semipermeable matrices of solid polymers containing the therapeutic agent. The various sustained-release materials available are well known by those skilled in the art. Sustained-release capsules may, depending on their chemical nature, release the particles over a range of several days to several weeks to several months.

The particles may also be co-administered with other well known therapeutic agents that are selected for their particular usefulness against the condition that is being treated. For example, such therapeutic agents can be pain relievers, blood thinners/anticoagulants, clot busters, stomach antacids, or compounds which lessen untoward effects of the particles.

The administration of these additional compounds may be simultaneous with the administration of the particles, or may be administered in tandem, either before or after the administration of the particles, as necessary. Any suitable protocol may be devised whereby the various compounds to be included in the combination treatment are administered within minutes, hours, days, or weeks of each other. Repeated administration in a cyclic protocol is also contemplated to be within the scope of the present invention.

Following administration of the particles, capture of the therapeutic particles by the implanted device is effectuated for a period of time. The duration of the magnetic particle delivery may be dependent on any number of variables, including without limitation, the species, breed, size, height, weight, age, overall health of the subject, the type of therapeutic agent, the composition of the particle, the mode or manner or administration, or the type or severity of the condition being treated. The appropriate effective amount of particles to use can be routinely determined by those of skill in the art using routine optimization techniques and the skilled and informed judgment of the practitioner and other factors evident to those skilled in the art. Preferably, a therapeutically effective dose of the particles described herein will provide therapeutic benefit without causing substantial toxicity to the subject.

The particle therapeutic regimen can be initiated with smaller dosages of particles, followed by an increase in dosage over the course of the treatment until the optimum effect under the circumstances is reached. If needed, the total daily dosage may be divided and administered in portions throughout the day.

For effective treatment of a particular condition, one skilled in the art may recommend a dosage schedule and dosage amount adequate for the subject being treated. It may be preferred that dosing occur one to four or more times daily for as long as needed. The dosage schedule may also vary depending on the active agent concentration, which may depend on the needs of the subject.

The inventive methods can be used to treat any condition that is amenable to targeting therapeutics. The methods are particularly well suited to treat vascular conditions, including follow up care for a metallic stent angioplasty.

The following examples are provided to describe the invention in greater detail. They are intended to illustrate, not to limit, the invention.

Example 1

Preparation of Non-Magnetic, Stabilized Nanoparticles Comprised of Anionic Lipid Salt Sodium oleate was formed by dissolving oleic acid (100 mg) in 5 ml aqueous solution containing 14.8 mg sodium hydroxide with gentle heating to 40° C. Albumin solution (10%, 0.4 ml) was added to the aqueous sodium oleate. Calcium chloride aqueous solution (111 mg in 5 ml) was added dropwise resulting in formation of nanoparticles exhibiting a characteristic bluish opalescence due to the Tyndall effect. The nanoparticle size was 230±20 nm as determined by photon correlation spectroscopy.

To prepare a stable aqueous suspension of mixed iron oxide (magnetite), ferric chloride hexahydrate and ferrous chloride tetrahydrate (100 mg and 50 mg, respectively) are dissolved in 4 ml deionized water and precipitated by 1.6 ml of aqueous sodium hydroxide (1 M). Sodium oleate (150 mg in 5 ml deionized water) is then added to the resulting precipitate. The magnetite precipitate is resuspended in the form of nanocrystals by heating under argon to 90° C. and ultrasonication (5 min each step) repeated twice to form a ferrofluid. Bovine serum albumin (200 µl, 10% w/v) is added as a stabilizer to 1 ml of the obtained sodium oleate solution containing oleate-stabilized colloidal magnetite, and nanoparticles are formed by dropwise adding calcium chloride (33.3 mM, 1.5 ml) upon gentle stirring. The particles are washed by sedimentation on a magnet and subsequently resuspended in water. The particles can also be stored lyophilized after freeze drying in 10% w/v trehalose solution as a cryoprotectant.

Figure 1B:
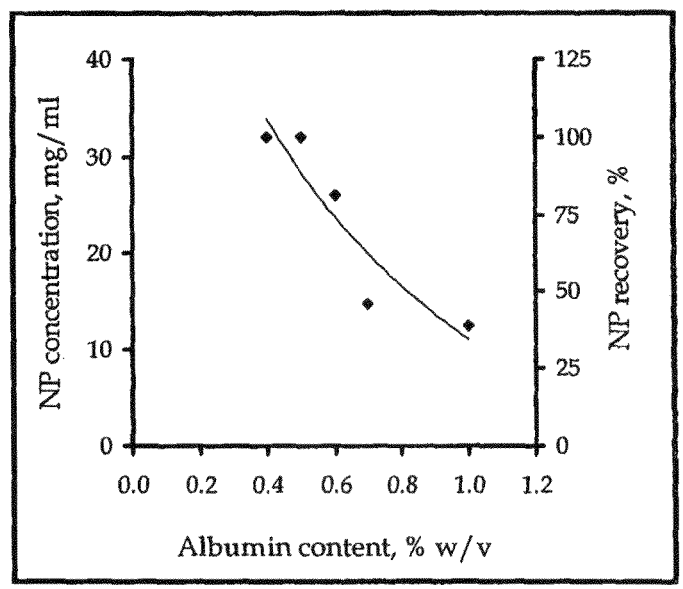

FIG. 1A shows that the size of the resultant nanoparticles can be adjusted by varying the concentration of the stabilizer. FIG. 1B shows that the yield of the resultant nanoparticles can be adjusted by varying the concentration of the stabilizer.

Example 2

Incorporation of a Neutral Lipohilic Agent into Magnetic Nanoparticles

This example shows the incorporation of a neutral lipophilic agent, such as taxol, into magnetic nanoparticles, by adding its concentrated solution in a small volume of a biocompatible water-miscible solvent, to the ferrofluid containing the anionic lipid and the stabilizer.

Taxol-loaded nanoparticles were prepared as in Example 1. Taxol, 1.0 mg in 10 µl dimethylformamide, was added to the ferrofluid containing the anionic lipid and the stabilizer and the nanoparticles isolated as in Example 1.

The effect of taxol-loaded magnetic nanoparticles in comparison to an equivalent dose of nanoparticles containing no drug on proliferation of cultured rat aortic smooth muscle cells following 15 min incubation under magnetic field (500 G) was determined using Alamar Blue assay ($\lambda_{excitation}$=540 nm, $\lambda_{emission}$=575 nm). The cells were seeded on a 96-well plate at 10% confluency, and the cell proliferation was measured after three days as a function of the drug formulation amount.

Figure 2:
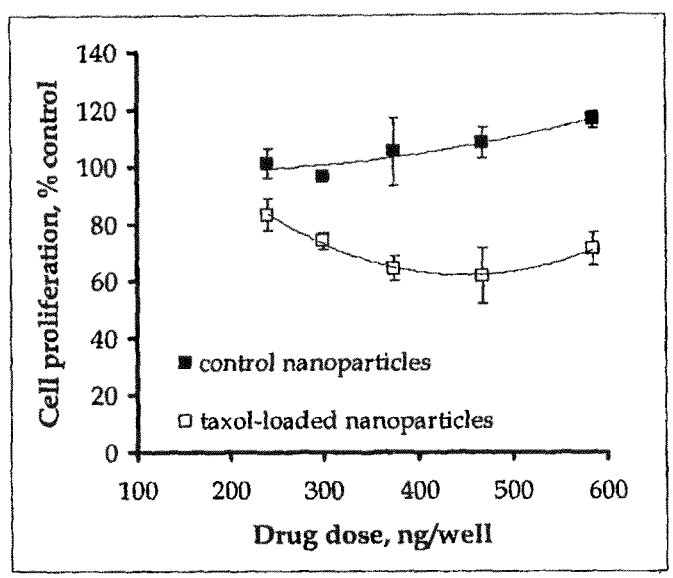
FIG. 2 shows the effect of taxol-loaded magnetic nanoparticles on the proliferation of cultured rat aortic smooth muscle cells as a function of the nanoparticle amount.
Figure 3A:
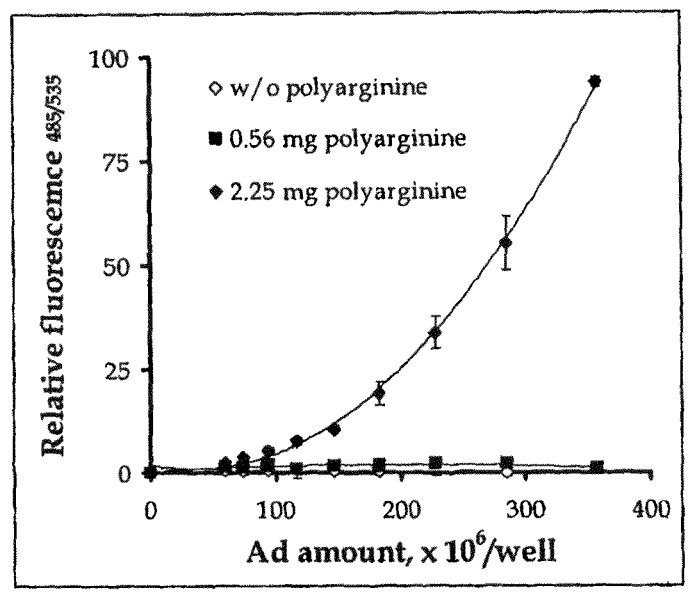
FIG. 3A shows transgene expression in cultured rat aortic smooth muscle cells as a function of the poly-L-arginine formulation amount and nanoparticle dose. 3B shows transgene (Green Fluorescent Protein, GFP) expression in bovine aortic endothelial cells as a function of the poly-L-arginine formulation amount and nanoparticle dose. 3C shows transgene expression in cultured endothelial cells as a function of magnetic exposure. 3D shows the kinetics of transgene expression in cultured endothelial cells treated with poly-L-arginine modified nanoparticles at a dose equivalent to 285× $10^6$ viral particles per well with or without a magnetic field.
Figure 3B:
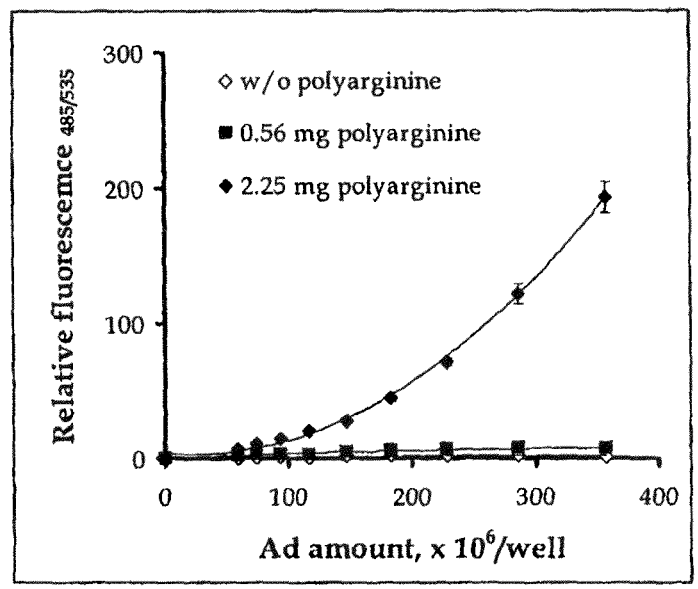
Figure 3C:
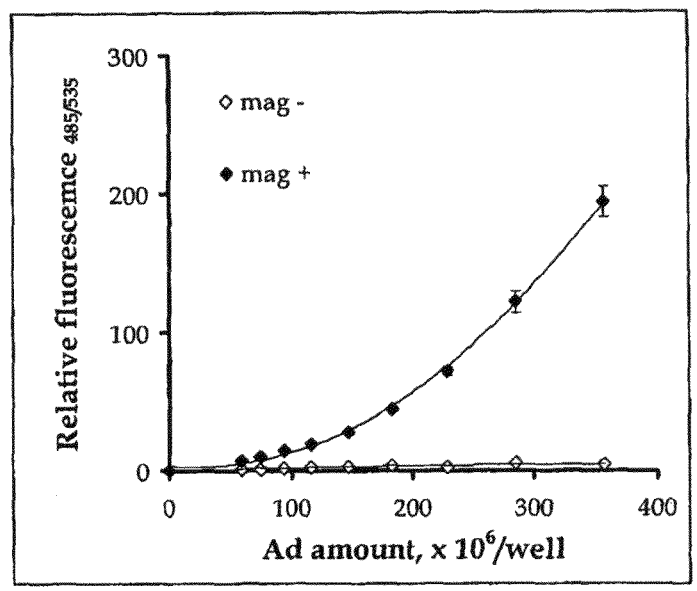
Figure 3D:
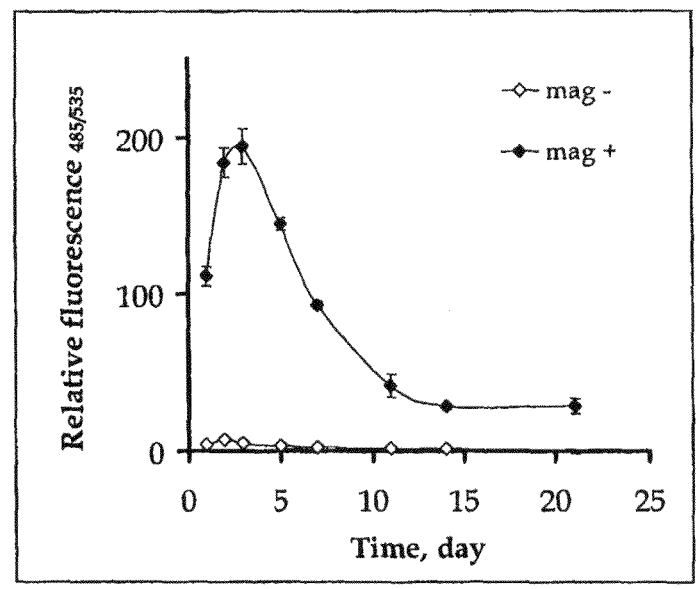

FIG. 2 shows the effect of taxol-loaded magnetic nanoparticles on the proliferation of cultured rat aortic smooth muscle cells as a function of the nanoparticle amount. As can be seen from this Figure, although the control nanoparticles have a weak stimulatory effect on the growth of smooth muscle cells, the proliferation of cells treated with taxol nanoparticles was inhibited in a dose dependent manner and decreased by ~30% at the highest dose applied compared to untreated cells.

Example 3

Preparation of All-Trans Retinoic Acid-Loaded Magnetic Nanoparticles

The formulation method described above is suitable for preparing nanoparticles with ionic compounds through their inclusion as their water-insoluble complexes. All-trans retinoic acid (atRA) sodium salt, an anticancer agent, is an anionic lipid that readily complexes with calcium, and provides an example of an ionic substance that can be incorporated into nanoparticles.

A formulation containing atRA was prepared as described in Example 2 with the following modifications. Magnetite aqueous dispersion was prepared in 4 ml water containing 100 mg sodium oleate. All-trans retinoic acid (50 mg) was dissolved in 1 ml aqueous of sodium hydroxide (6.7 mg) and added to the magnetite dispersion prior to the dropwise addition of calcium chloride in the presence of albumin.

Example 4

Preparation of Adenovirus Containing Magnetic Nanoparticles

Magnetic nanoparticles encapsulating adenovirus can be produced by adding adenovirus prior to the nanoparticle formation step either in the sodium oleate solution containing ferrofluid, or in the calcium solution. In the following examples 50 μl of adenovirus ($5 \times 10^{12}$ particles per ml) encoding for green fluorescent protein (GFP) were added to the ferrofluid to accomplish adenovirus entrapment in the particles.

Adenovirus-impregnated nanoparticles were applied to confluent smooth muscle cells seeded on 96-well plates at doses equivalent to 60-285 million viral particles per well for 30 min with or without a magnetic field. The gene expression was assayed by measuring GFP fluorescence ($\lambda_{excitation}$=485 nm, $\lambda_{emission}$=535 nm) in cells 3 days post treatment.

Example 5

Formation of Magnetic Nanoparticles in the Presence of a Cationic Peptide

A further improvement in the transduction efficiency can be achieved by co-addition of one or more cationic peptides or proteins, in particular arginine-rich polypeptides and proteins, such as poly-L-arginine or protamine, to the calcium chloride solution. Nanoparticle modification with these peptides and proteins facilitates the cellular uptake and therefore results in a more efficient internalization of the encapsulated adenovirus with a resultant increase in transgene expression. Incorporating poly-L-arginine hydrochloride (molecular weight ~70,000 Da) in the nanoparticles results in a dose dependent increase in adenoviral gene transfer both in cultured rat aortic smooth muscle cells and bovine aortic endothelial cells.

The cells were seeded at confluence on 96-well plates and treated for 15 min in the presence of a magnetic field with increasing doses of adenovirus-impregnated nanoparticles (290±20 nm) prepared with addition of 0-2.25 mg poly-L-arginine hydrochloride. The expression of GFP was measured fluorimetrically on day three.

FIG. 3 shows transgene expression in cultured rat aortic smooth muscle cells and bovine aortic endothelial cells (FIG. 3A and FIG. 3B, respectively) as a function of the poly-L-arginine formulation amount and nanoparticle dose. Transgene expression in cultured endothelial cells with and without magnetic exposure is shown in FIG. 3C. The kinetics of transgene expression in cultured endothelial cells treated with poly-L-arginine modified nanoparticles at a dose equivalent to $285 \times 10^6$ viral particles per well with or without a magnetic field is shown in FIG. 3D. In the absence of a magnetic field substantially lower gene transfer rates were observed as shown here for cultured endothelial cells (FIG. 3C).

Example 6

Magnetic Gradient Targeting of Nanoparticles

Figure 6A:
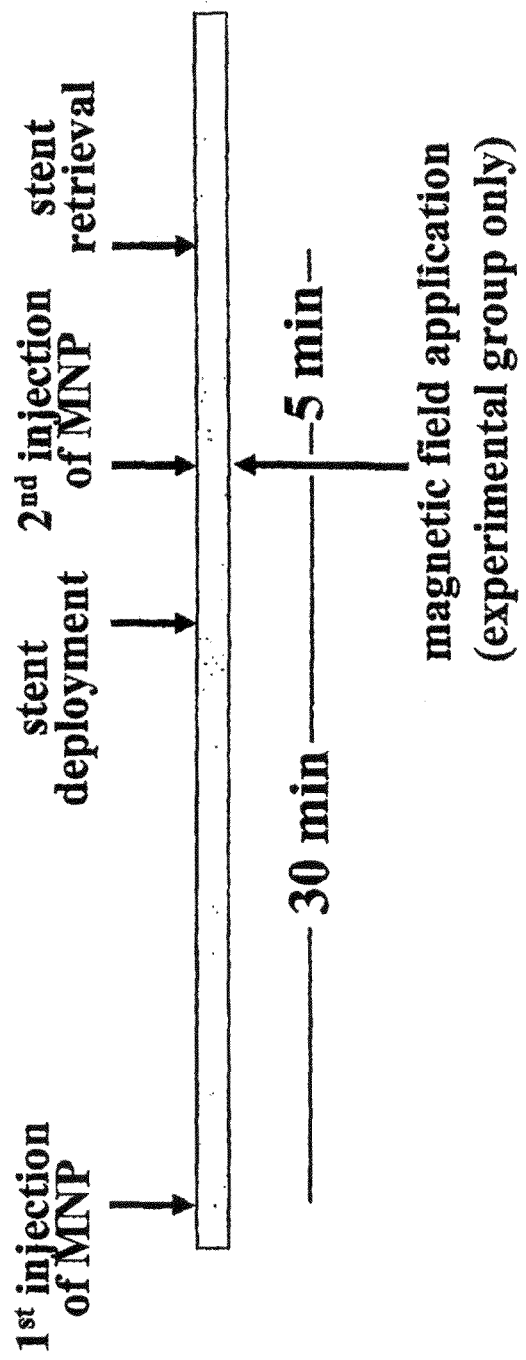
FIG. 6A summarizes an exemplary embodiment of the magnetically assisted therapeutic system, in which albumin modified magnetic carrier nanoparticles with a red fluorescent label were injected into a rat having an intravascularly implanted steel stent.

Albumin modified magnetic nanoparticles with a red fluorescent label were injected into the tail vein of a rat with an already deployed 6 mm-long Grade 304 Stainless Steel stent (FIG. 6A). Grade 304 Stainless Steel ("304 steel") has a history of use in implantable devices. Although there are no commercially available stents made out of 304 steel, a stent design was created and contracted to a medical device company to fabricate a set of these stents for use in the experiments. Thus, all of the studies reported here did not use any of the currently commercially used stents.

The 304 stent in these rat studies was investigated both with and without a magnetic field across the stent. In addition, magnetic nanoparticles without a stent were also injected into animals, with investigations to see if there was any localization that took place without stent deployment.

Methods: Paclitaxel was dispersed within the polylactic acid (PLA) matrix of magnetite-loaded nanoparticles (MNP). Adenovirus-tethered MNP were prepared using photochemical surface activation with the subsequent attachment of a recombinant adenovirus binding protein, D1, followed by formation of nanoparticle-adenovirus complexes. Plasmid vectors were charge-associated with PEI-functionalized MNP. Magnetic trapping of MNP on the steel meshes and stents under different field strength and flow conditions was studied in a closed circuit flow system. Transfection/transduction using gene vectors associated with magnetic nanoparticles was studied in smooth muscle (SMC) and endothelial cells. Magnetic force-driven localization of reporter gene-associated MNP and MNP-loaded cells on pre-deployed stents and resulting transgene expression were studied a rat carotid stent model.

Protocol (FIG. 6A): Four hundred μl of magnetically responsive fluorescent labeled, polylactic acid based magnetite-loaded nanoparticles were intravenously-injected (through the tail vein) upon induction of anesthesia in 480-510 g rats (Sprague-Dawley rats (n=6)). The magnetite-loaded nanoparticles were 350 nm, consisting of 7.2 mg per injection. This injection was carried out to saturate the reticulo-endothelial system of the animal to prevent excessive capturing of the second main dose of nanoparticles in liver and spleen.

Within 30 minutes of the first injection, a 304 steel stent was deployed in the left common carotid artery. Immediately after that, another 400 μl dose of the nanoparticles was injected intravenously, either with or without 300 G magnetic field created by 2 electromagnets placed adjacent to the neck of the animal. The field was maintained for 5 min after injection, after which the arteries were harvested. The stents were removed and nanoparticles deposition on stents and luminal aspects of arteries was examined by fluorescence microscopy. After acquisition of respective images BODIPY-labeled (red fluorescent) PLA was extracted in acetonitrile and its concentration was determined fluorimetrically against a calibration curve. For fluorescence control/background purposes in one additional rat no nanoparticles were injected and the stented arteries were removed and similarly processed to obtain background fluorescence values.

Results: In a closed circuit flow system MNP and cells loaded with MNP were trapped on magnetic meshes with exponential kinetics. Rat aortic SMC (A10) cultured on 316L stainless steel grids showed 100-fold increased gene transduction when exposed to the MNP-Ad$_{GFP}$ compared to controls. Paclitaxel MNP demonstrated inhibition of A10 cells growth in culture. Systemic intravenous injection in rats of MNP resulted in 7-fold higher localization of MNP on intra-arterial stents compared to controls when carried out in the presence of external magnetic field (300-G).

Figure 6B:
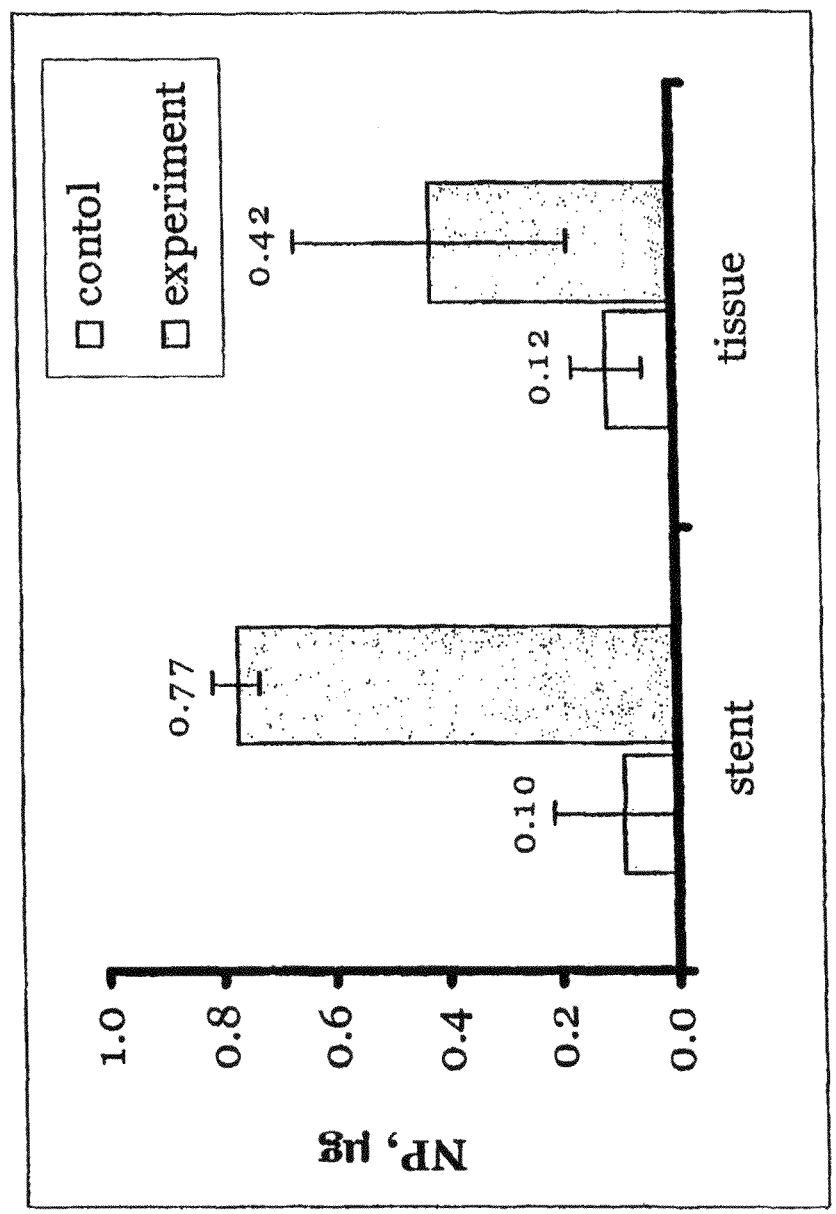
FIG. 6B summarizes results of the therapeutic agent delivery, for sequestering in the implanted device.

The results of these studies are shown in FIG. 6B (fluorimetry, 540/575 nm), as well as with fluorescent microscopy (not shown), demonstrating intense localization of magnetic nanoparticles to the deployed 304 stent, and also localization of magnetic nanoparticles to the arterial wall directly proximal to the stent. In addition, using a specific fluorescent assay, the significant localization of magnetic nanoparticles following intravenous injection using this methodology was quantified.

Conclusion: Magnetically targeted drug/gene delivery using high field gradients to stented arteries offers great promise because of the potential for not only initial dosing, but repeated administration utilizing magnetic field-mediated localization of vectors to the stented arterial wall. These results clearly demonstrate a significantly higher nanoparticles deposition on stents and adjacent arterial tissue in the group where systemic intravenous delivery was carried out in conjunction with an electromagnetic field compared to "no field" controls. Non-stented arteries demonstrated no nanoparticle localization with or without a magnetic field.

Example 7

Magnetic Trapping and Removal of Residual Nanoparticles and Cells

Figure 7:
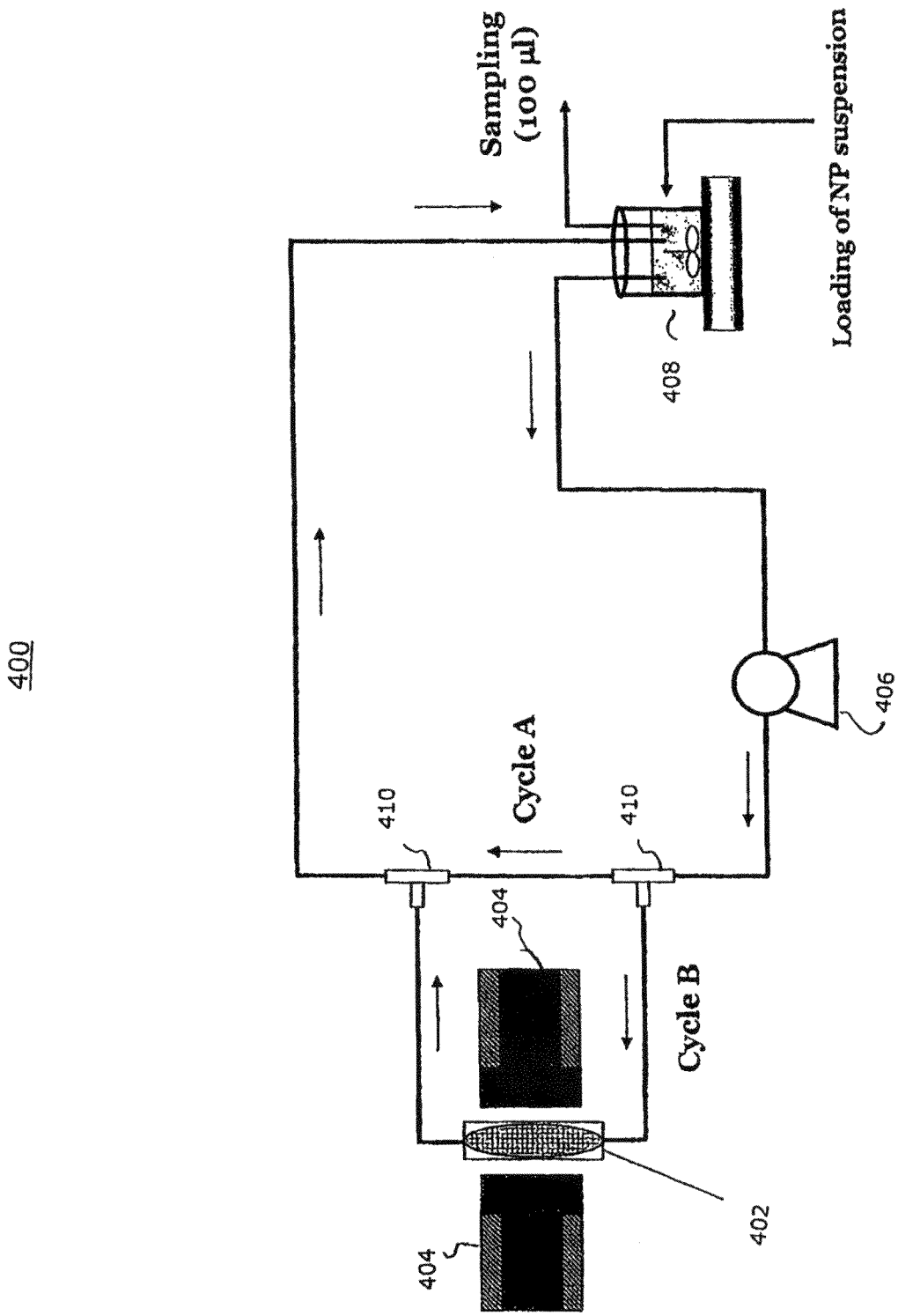
FIG. 7 summarizes schematically the retrieval system shown in FIG. 5 that is used to model the retrieval of magnetic carrier nanoparticles or cells from the cardiovascular circulation cycle.

This Example illustrates removal of residual nanoparticles and cells with an external magnetically responsive steel filter ("magnetic trap"). FIG. 7 illustrates a flow system 400 that schematically summarizes the retrieval system 108 (FIG. 4) that is used to model the retrieval of magnetic nanoparticles or cells from the circulation. As shown in FIG. 7, flow system 400 includes a magnetic trap 402 (an Eppendorf with 430 stainless steel mesh for capturing of the residual nanoparticles), electromagnets 404 for generating a magnetic field, a peristaltic pump 406, a stirrer 408, and faucets 410 for directing flow to cycle A or cycle B. A suitable peristaltic pump 406, stirrer 408, and faucets 410, as commonly for an apheresis apparatus, will be understood by the skilled person from the description herein.

The following experimental protocol was used to determine the kinetics of magnetic nanoparticles and cell capture, respectively, using the "Magnetic Trap" apparatus.

PLA-PEG based magnetic nanoparticles were diluted in 50 ml of 5% glucose solution and filtered (5 μm cut-off) to ensure uniform particle size. Alternatively, bovine aortic endothelial cells (BAEC) were grown to confluence and incubated with fluorescently labeled magnetic nanoparticles on a cell culture magnet (Dexter Magnet Technologies, Elk Grove Village, Ill.) producing a strong magnetic field (500 Gauss) for 24 hours, followed by cell washing and resuspension in fresh cell culture medium. Untreated cells were used as a control.

The flow system 400 was purged with 5% glucose or cell culture medium, respectively, (washing step) followed by one cycle of nanoparticle/cell suspension in the loop A to equilibrate the system (priming step). Next, nanoparticle/cell suspension was redirected to the loop B including the trapping device 402 equipped with one or three 430 stainless steel mesh pieces (total weight of 0.30±0.01 and 0.83±0.05 g, respectively) and an external magnetic field of 800 Gauss generated by two solenoid electromagnets 404. A $t_0$ sample was withdrawn and further used as a reference (100% of NP/cells). Additional samples were collected at predetermined time points during 2.5 hours and 35 min in the nanoparticles and cell retrieval experiments, respectively. The effect of the magnetic field exposure was investigated in comparison to "no field" conditions employed during the first 25 and at 3 minutes into the experiment for the nanoparticles and cells, respectively, after which the field was applied. A NP/cell fraction remaining in the circulation at a given time point was determined fluorimetrically ($\lambda_{ex}$=540 nm, $\lambda_{em}$=575 nm) in relation to the reference sample. The mesh samples were visualized under the fluorescent microscope using red fluorescence filter set (540/575 nm) immediately and 24 hours after completing the experiment. Collected cells were incubated overnight at 37° C. and their morphology was examined microscopically.

Figure 8:
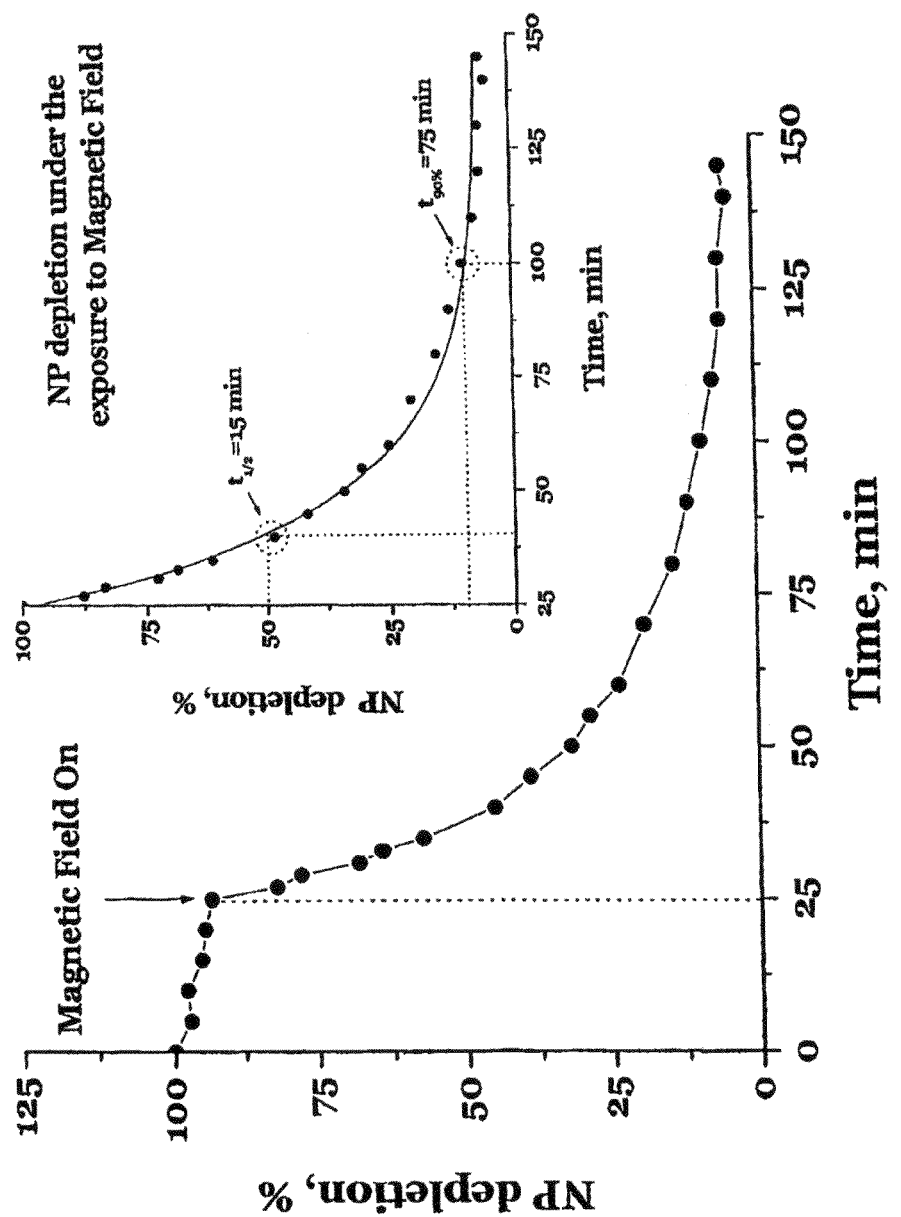
FIG. 8 summarizes exponential depletion kinetics of carrier nanoparticles under the influence of a magnetic field gradient.
Figure 9:
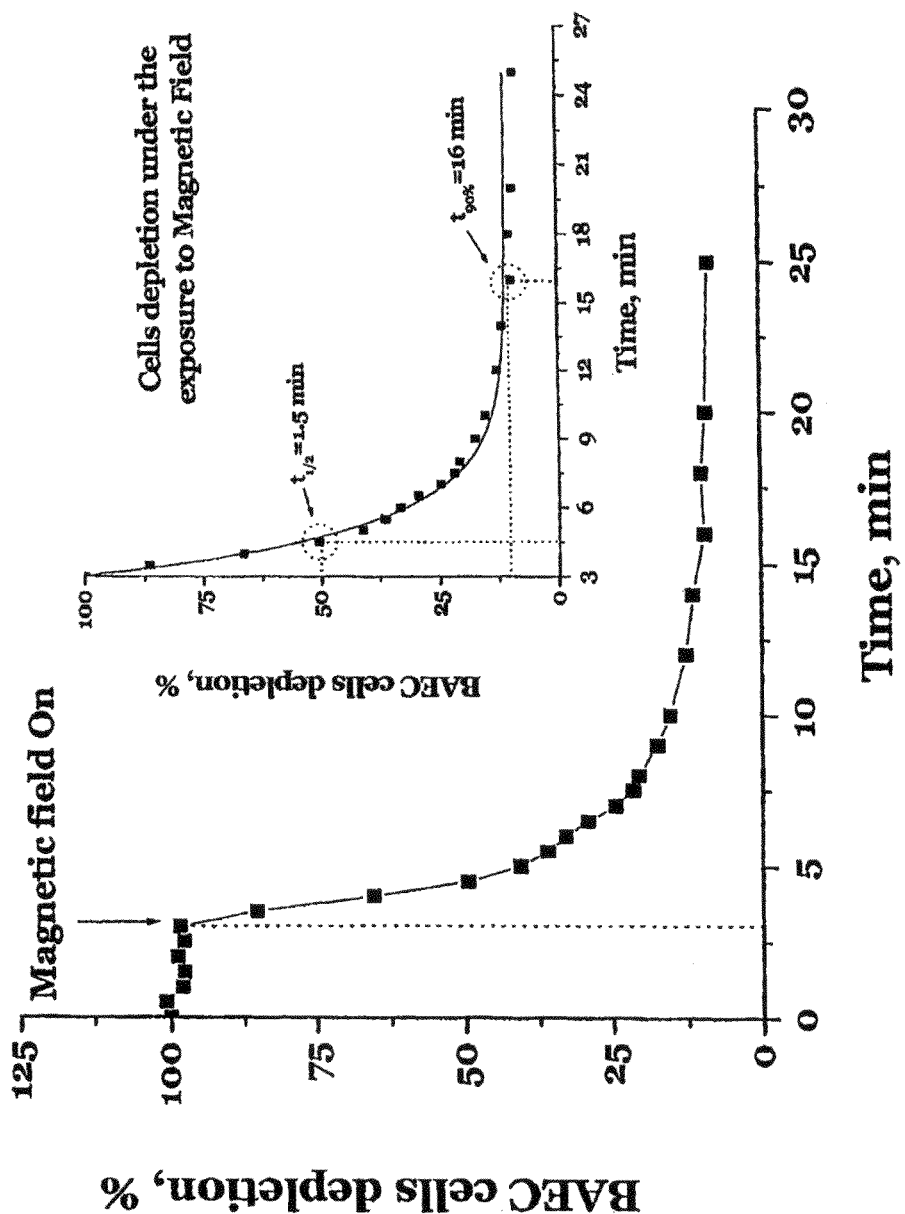
FIG. 9 summarizes exponential depletion kinetics of carrier cells under the influence of a magnetic field gradient.

FIG. 8 and FIG. 9 depict exponential depletion kinetics of nanoparticles and BAEC cells, respectively, over time under the influence of a magnetic field. A significantly less pronounced decrease in both nanoparticles and BAEC cells is also observed in "no field" conditions. Under the magnetic field exposure, the depletion kinetics of both nanoparticles and cells was very fast with $t_{90\%}$ (i.e., time required to eliminate 90% of the circulating nanoparticles or cells) equaling 75 min and 16 min for nanoparticles and cells, respectively. The five-fold lower $t_{90\%}$ for cell capture is apparently due to their higher magnetic responsiveness due to the cells containing a large number of nanoparticles/cell compared to that of the smaller sized NP.

Figure 10:
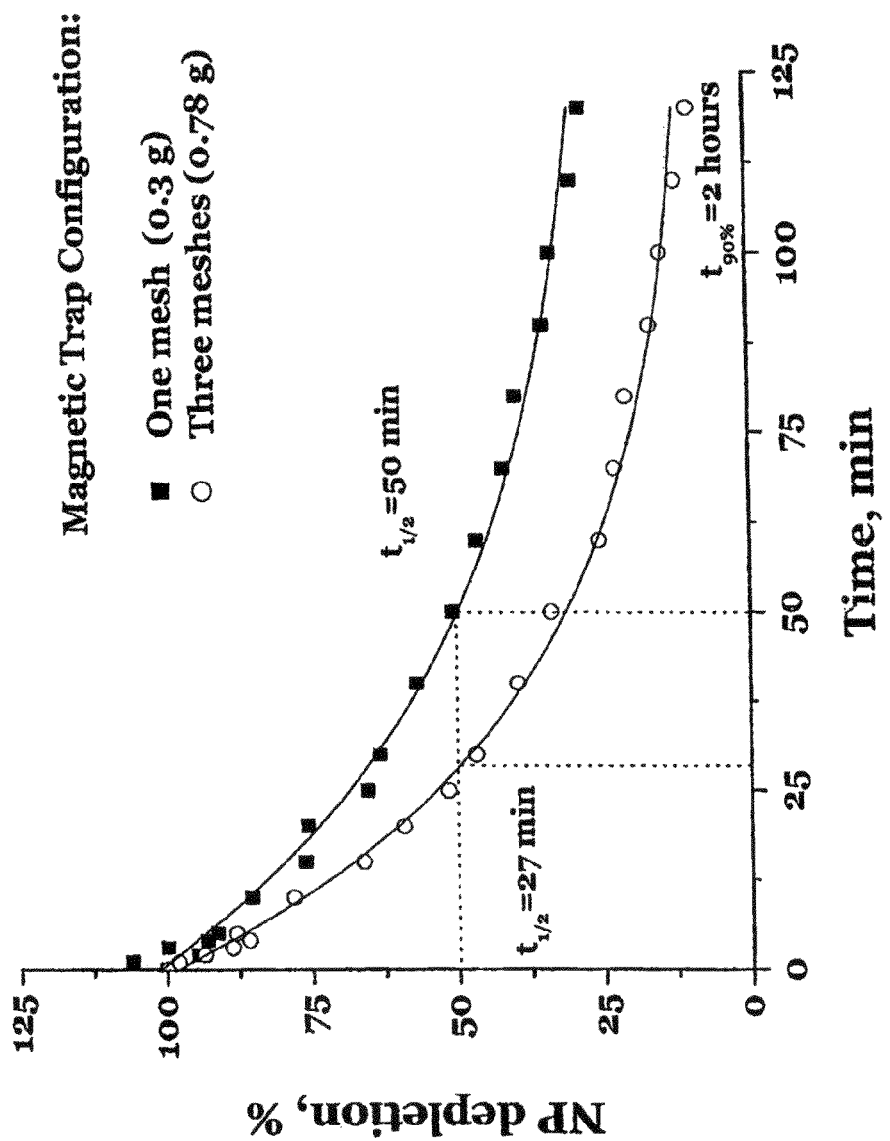
FIG. 10 summarizes how different magnetic sequestering configurations, for performing the exemplary method shown in FIG. 5, affect depletion kinetics.

Referring to FIG. 10, different magnetic trap configurations and corresponding depletion kinetics are shown. Increasing the amount and surface area of the 430 stainless steel in the "Magnetic Trap" from 0.3 to 0.83 g, caused a significant decrease in the circulation $t_{1/2}$ of the nanoparticles (27 vs. 50 min). Thus, optimization of the "Magnetic Trap" design could potentially allow for nanoparticles and cell retrieval kinetics sufficiently fast for its clinical use. Spreading of cells was also demonstrated where the cells were removed from the circulation for measurement of cell depletion. Cells were grown overnight on the cell culture plate at the 37° C. and in the atmosphere of 5% of $CO_2$. Micrographs of the mesh taken post experiment demonstrated nanoparticles deposited on the "Magnetic Trap."

Magnetically responsive cells captured at the end of the experiment and spreading of the cells 24 hours later were also demonstrated. Cells sampled from the circulation during the cell capture experiment demonstrate normal morphology characteristic of BAEC. The growth conditions are 10% FBS supplemented DMEM at 37° C. and 5% $CO_2$. The meshes used in the magnetic trap in this experiment were visualized under the fluorescent microscope immediately and 24 hours post experiment in order to evaluate the morphology of the captured cells. A high number of cells are shown to be initially captured by the edges of the mesh, of which those located most adjacent to the mesh surface form a layer of uniformly spread cells after 24 hours over the expanse of the entire surface of the mesh framework thus showing the viability of the magnetically targeted cells. Capture of magnetic carrier nanoparticles at the end of experiment was demonstrated on the surface of the 430 stainless steel mesh under the field of 800 Gauss ("The Magnetic Trap"), as compared with a control mesh at the beginning of the experiment before application of magnetic field.

Example 8

TEM and Magnetization Curve of Albumin-Stabilized Magnetic Nanoparticles

Figure 11A:
FIGS. 11A and 11B summarize results of transmission electron microscopy and magnetic moment versus magnetic field (magnetization curve) for Albumin-stabilized superparamagnetic nanoparticles (MNP).
Figure 11B:
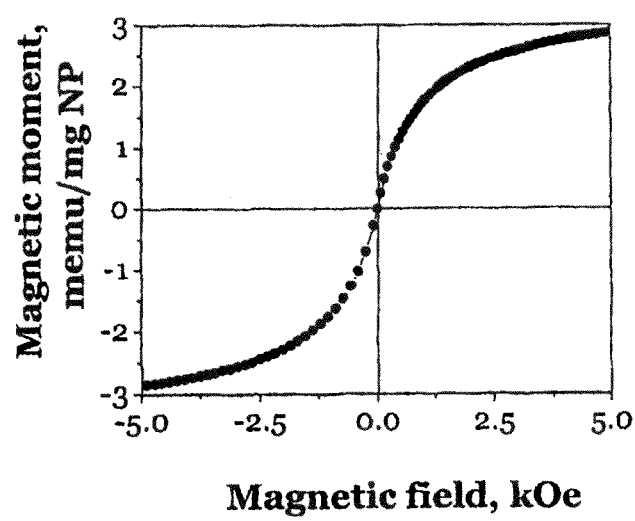

Referring now to FIGS. 11A and 11B, results from transmission electron microscopy and a magnetization curve (magnetic moment versus magnetic field) are shown, respectively for Albumin-stabilized magnetic nanoparticles (MNP), described above with respect to Example 6. Note the small size and the large number of individual oleic acid coated magnetite grains distributed in the MNP polymeric matrix (FIG. 11A). MNP exhibits a superparamagnetic behavior, showing no significant hysteresis, and a remnant magnetization on the order of 0.5% of the respective saturation magnetization value (FIG. 11B).

Example 9

MNP Cell Loading

Figure 12A:
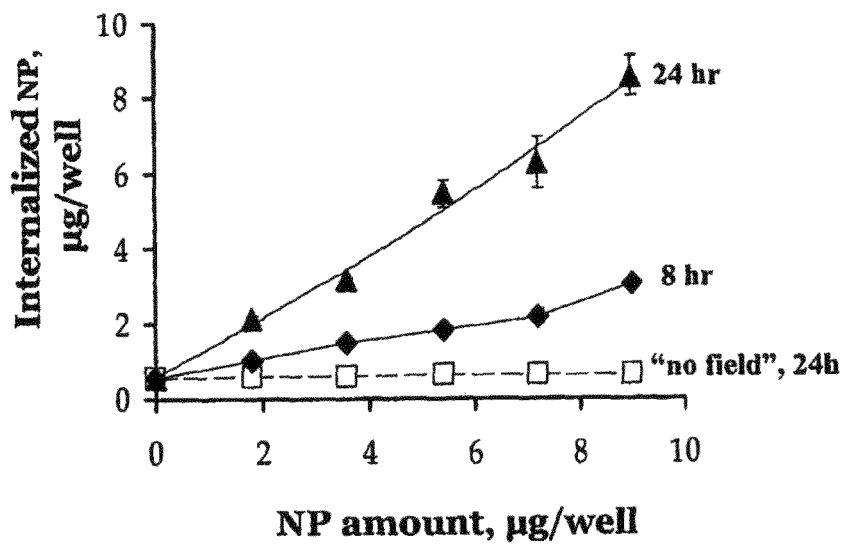
FIG. 12A-12B summarize in vitro MNP cell loading studies with respect to the kinetics of MNP uptake and viability of cells loaded with MNP.
Figure 12B:
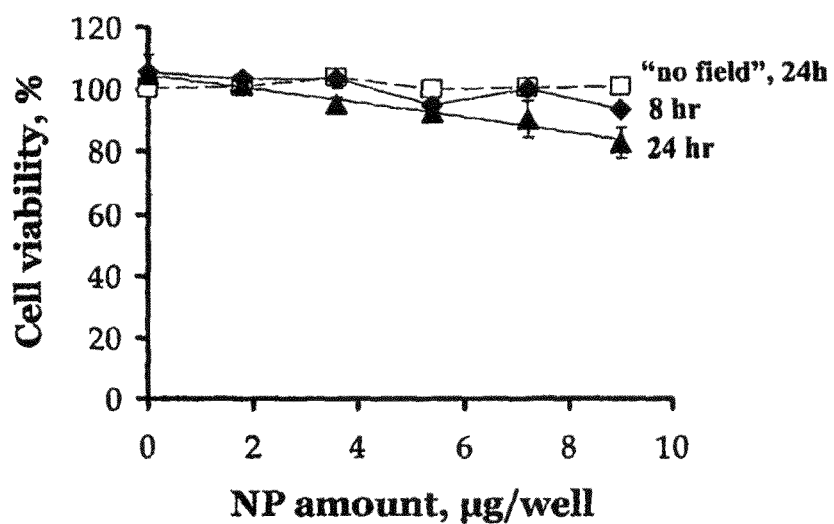

Referring now to FIGS. 12A-12B, in vitro MNP cell loading studies are illustrated. In particular, FIG. 12A illustrates kinetics of the MNP uptake by bovine aortic endothelial cells (BAEC) as a function of MNP dose and incubation time; FIG. 12B illustrates cell viability as a function of MNP dose and incubation time; and FIG. 12C illustrates a magnetization curve of cells loaded with MNP demonstrating superparamagnetic behavior as was observed with MNPs per se. The nanoparticles uptake was determined by fluorescence of internalized MNPs. Cell survival was determined by Alamar Blue assay.

BAEC (bovine aortic endothelial cells) were incubated with various doses of MNP on a magnet. As shown in FIG. 12A, the MNP uptake was determined at different time points by fluorescence of internalized nanoparticles. The amount of internalized MNP was near linearly dependent on the nanoparticle dose. Approximately 30% of internalization was observed after 8 hours and the uptake was practically complete after 24 hours, whereas no significant uptake was achieved in the absence of a magnetic field at 24 hr. As shown in FIG. 12B, cell viability at different experimental conditions (incubation time and MNP dose) was not adversely affected by MNP loading. Greater than 85% of cell survival was observed at all studied MNP doses and incubation times relatively to untreated cells. As shown in FIG. 12C, the magnetization curve of cells loaded with MNPs demonstrating super-paramagnetic behavior showing no significant hysteresis and a remnant magnetization on the order of 0.5% of the respective saturation magnetization value.

Example 10

Gene Transfer Efficiency and Cell Toxicity

Figure 13A:
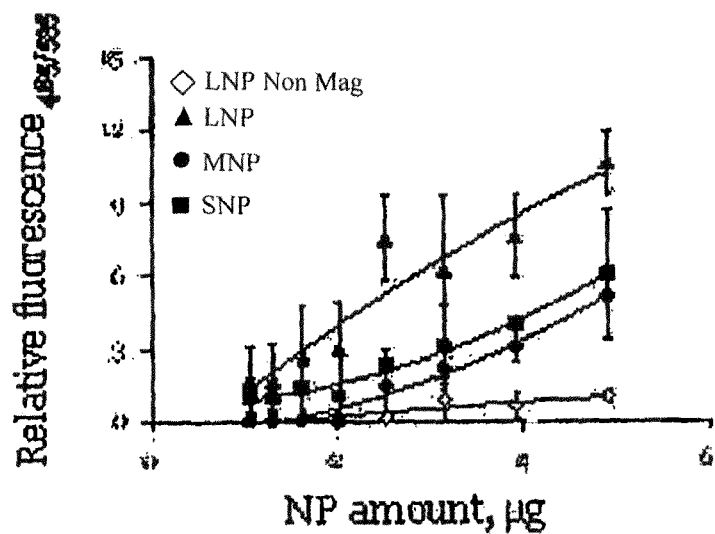
FIG. 13A shows reporter gene transfer mediated by polyethylenimine-coated MNP combined with DNA encoding green fluorescent protein (GFP) presented as GFP fluorescence at λem/λex of 485 nm/535 nm as a function of a nanoparticle amount in A10 cells, wherein iron oxide-loaded nanoparticles were prepared using 0 ml THF (large nanoparticles, LNP), 3 ml THF (medium nanoparticles, MNP), or 4.5 ml THF (small nanoparticles, SNP) in the organic phase, versus large nanoparticles without iron oxide (LNP Non Mag, used herein as a control). 13B shows the relative fluorescence measured at 485 nm/535 nm as a function of a nanoparticle amount in BAEC cells. 13C shows internalization of fluorescent (far red) labeled nanoparticles expressed as the relative fluorescence measured at 650 nm/670 nm as a function of a nanoparticle amount in A10 cells. 13D shows the relative fluorescence measured at 650 nm/670 nm as a function of a nanoparticle amount in BAEC. 13E shows cell survival as a function of a nanoparticle amount in A10 cells. 13F shows cell survival as a function of a nanoparticle amount in BAEC cells.
Figure 13B:
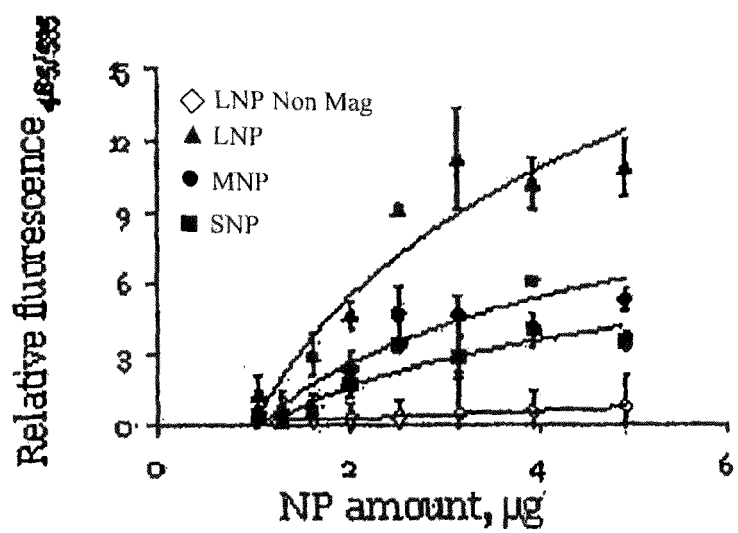
Figure 13C:
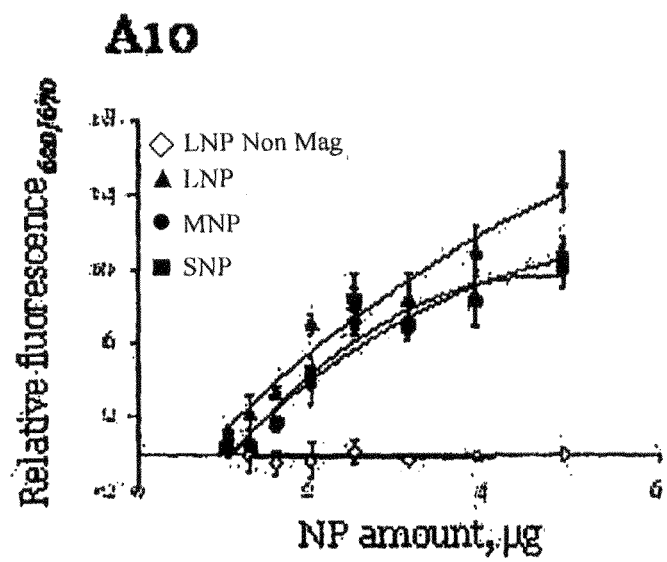
Figure 13D:
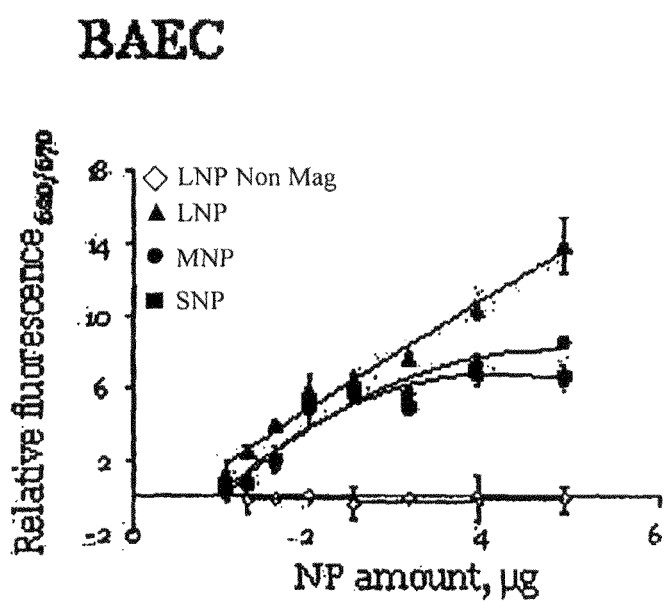
Figure 13E:
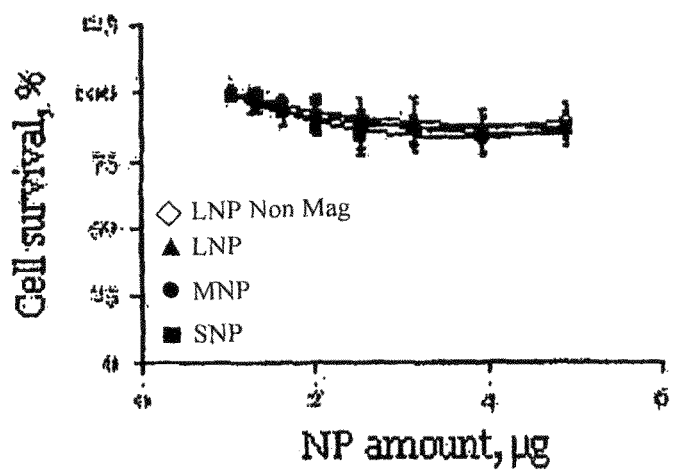
Figure 13F:
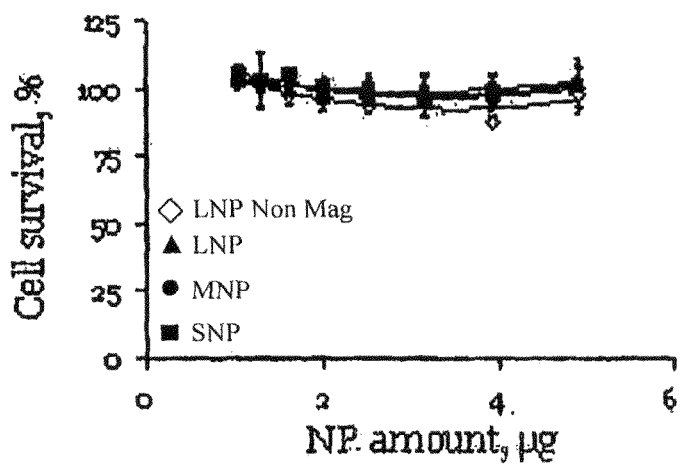

Particles were studied for transfection of cells in culture. Three kinds of magnetically responsive particles were prepared and complexed with DNA at different PEI:DNA ratios. In all experiments, nanoparticles were complexed with 0.25 µg GFP-encoding DNA plasmid per well in 5% glucose for 30 min, then mixed 1:4 with cell culture medium supplemented with 10% fetal bovine serum (FBS) and applied to cells for 10 min with magnetic field. Their transfection efficiency, as well as nanoparticles uptake and toxicity, was studied in cultured rat aortic smooth muscle and bovine aortic endothelial cells (A10 and BAEC, respectively) using non-magnetic particles as a control. Gene expression, NP uptake and cell survival were determined by measuring fluorescence at 485/535 nm, 620/670 nm and with the Alamar Blue assay (540/575 nm), respectively, at 2 day time point. The results are presented in FIG. 13A-F. Magnetically responsive formulations resulted in high levels of gene product as opposed to non-magnetic nanoparticles (FIGS. 13A-F) in correlation with their cellular uptake (FIGS. 13C and D). All formulations exhibited low toxicity in cell culture in the examined amount range (FIGS. 13E and F).

In another experiment, bovine aortic endothelial cells (BAEC) were seeded on day-1 ($2\times10^4$/well, on four 24-well plate). The cells were washed 2 times ($2\times1$ hr) with the 10% FBS-supplemented Dulbecco's Modified Eagle's Medium (DMEM) on day 0 prior to transfection. Plasmid DNA was incubated for 30 minutes with magnetic nanoparticles (the complexants) at various ratios in 5% w/v glucose solution, serially diluted 1.25-fold with FBS-containing DMEM to provide a final serum concentration of 10% or 80% and applied to cells at 0.25 µg DNA/well. The cells were incubated at 37° C., while one plate was placed at a time on the magnet (15 min), and another kept at a distance from it. The medium was then replaced with fresh pre-warmed DMEM supplemented with 10% FBS. The cells were observed for transfection after 24 hr.

The nanoparticles and PEI showed comparable transfection of BAEC cells in culture with DNA encoding for green fluorescent protein when applied without use of external magnetic field, whereas the transfection efficacy of the magnetic nanoparticles applied in the presence of a permanent magnet was substantially increased as compared to both control formulations and the magnetic nanoparticles applied in the absence of the magnet.

Similar effect of the magnetic field on the transfection efficacy was also observed in A10 cells in culture.

Notably, the magnetic NP were able to effectively transfect cells in presence of 10% and 80% serum apparently due to their protective effect against DNA enzymatic degradation, whereas practically no transfection was found when DNA:PEI complex was added to the cells in the presence of serum for the same time period.

Example 11

Magnetic Targeting of siRNA-Containing Nanoparticles

Magnetic nanoparticles were formulated using following protocol: 5.5 ml of an aqueous solution containing 300 mg $FeCl_3$ hexahydrate and 150 mg $FeCl_2$ tetrahydrate was rapidly missed with 4.75 ml aqueous solution of NaOH (1.0 M). The obtained precipitate was separated on a magnet. Oleic acid (150 mg) was added dropwise, the precipitate was suspended in 2 ml ethanol, and the mixture was degassed in argon. The contents were heated to 90° C. in a water bath for 5 min with several stirrings. 4 ml water was added dropwise upon gentle stirring, the oleic acid-coated iron oxide was precipitated on a magnet, and the liquid phase was carefully aspirated. The precipitate was washed with 4 ml ethanol to remove excess oleic acid; ethanol was aspirated following sedimentation on a magnet. The precipitate was resuspended in 5 ml chloroform.

An organic phase consisting of 200 mg polylactic acid (PLA) (D,L-PLA 70-120 K Sigma), 100 mg polyethylene-imine (PEI) (branched PEI, Aldrich 25 K) or 200 mg of linear PEI 200K (pH 7) and 100 mg oleic acid dissolved in the chloroformic suspension of magnetite was added to 15 ml deionized water pre-cooled in an ice bath, and the mixture was emulsified by sonication. The organic solvent was removed by rotavaporation at 25° C. The particles were filtered through 1.0 µm glass fiber filter and dialyzed against deionized water at 4° C. for 24 hr with several water replacements using 300,000 Da cut-off dialysis membrane. Trehalose (10% w/v) was added to the obtained nanoparticle suspension, and nanoparticles were lyophilized and stored at −20° C.

Figure 14:
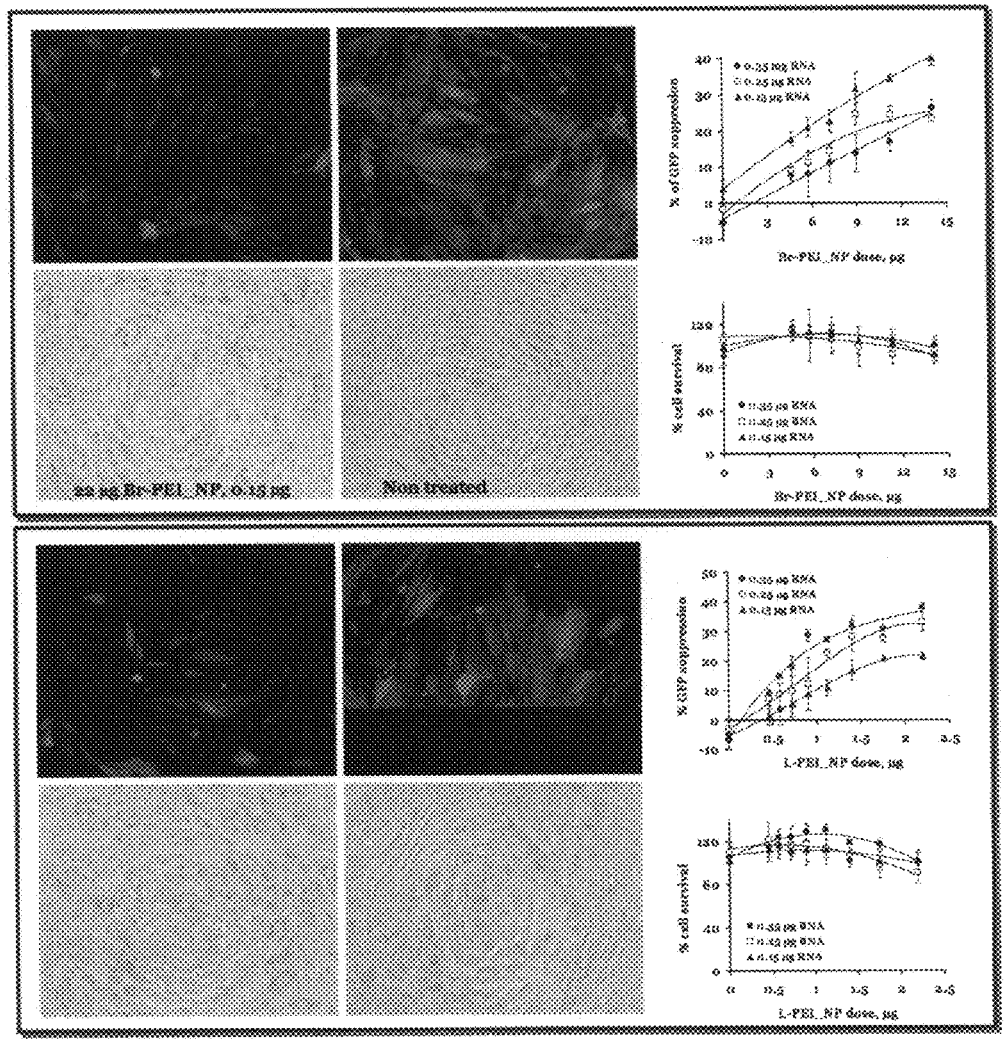
FIG. 14 shows suppression of eGFP expression in lentivirus-transduced smooth muscle cells (A10) by siRNA delivered with magnetic nanoparticles in the presence of a magnetic field (500 Oe).

The NP formulation (FIG. 14) used in the present example, diameter 360 nm, exhibited superparamagnetic behavior showing no significant hysteresis, and a remnant magnetization in the order of 0.5% of the respective saturation magnetization values. The magnetic moment depended near-linearly on magnetic field up to 1000 Oe reaching 66-68% of the saturation value, while a comparatively low increment in magnetization was observed upon further increasing the field to 5000 Oe (FIG. 14). The specific magnetic susceptibility of the NP was found to be about 5.03+0.04 emu/cm3×kOe.

The linear PEI was prepared as described in: Thomas, M et al. (2005). Proc. Natl. Acad. Sci. USA 102:5679-84. In brief, fully deacylated linear PEI 200K was prepared by the acid-catalyzed hydrolysis of the commercially available 200K PEOZ poly(2-ethyl-2-oxazoline) (Sima-Aldrich). Typically, 3.0 g of the PEOZ was added to 120 ml of 24% (w/v) HCl, followed by refluxing for 96 h. the first reaction mixture contained a white precipitate throughout the reaction. The PEOZ crystals dissolved completely in ~2 hr, but filtration, washed once with 2-propanol. The powder was redispersed in 2-propanol for 2 hours, isolated by filtration and dried under reduced pressure. The resultant white powder was confirmed by $^1$H-NMR to be pure PEI hydrochloride. The fully deacylated PEI 200 exhibited a singlet at 3.57 ppm by NMR corresponding to —$CH_2$—$CH_2$—$NH_2^+$ but no signal corresponding to the N-propionyl moieties, confirming their complex removal.

Suppression of eGFP expression in lentivirus transduced smooth muscle cells by siRNA using magnetic NP was achieved in the following experiment: Rat aortic smooth muscle cells (A10) were cultivated for several passages after their transduction with GFP encoding lentivirus. Cells were grown in DMEM medium supplemented with $10^5$ fetal bovine serum (FBS). Lyophilized NP were resuspended in 100 µl of deionized water and diluted serially in triplicates to achieve following NP amount range: 0-14 µg and 2.2 µg for branched and linear PEI-NP per well (96-well plate format) respectively. siRNA was incubated for 30 min with NP at various ratios in 5% w/v glucose solution and added to cells after 5-fold dilution with serum supplemented DMEM at 0.15, 0.25, and 0.35 µg RNA/well followed by 20 min exposure to magnetic field (500 Gauss produced by a cell culture magnet, Dexter Magnet Technologies, Elk Grove Village, Ill.). Fluorimetric measurements of GFP expression ($\lambda$em $\lambda$ex=485 nm/535 nm) and cell viability (AlamarBlue assay [Biosource, Camarillo, Calif. USA], ($\lambda$em $\lambda$ex=540 nm/575 nm) were performed in live cells 5 days post treatment.

Efficient eGFP suppression was achieved using magnetic NP formulated with either branched or linear PEI (FIG. 14). For both formulation types the eGFP suppression depended directly on the NP dose, reaching maximum of 20-40% (FIG. 14). However, the eGFP suppression achieved using linear PEI formulation exhibited saturation with increasing NP dose, while for branched PEI-NP formulation the eGFP suppression exhibited near-linear dose dependence in the entire studied NP range. The suppression of eGFP was directly siRNA dose dependent in the case of the linear PEI formulation and inversely dependent for branched PEI-NP formulation resulting in a maximal suppression of 38 and 40% for linear and branched PEI formulations at a dose of 0.35 and 0.15 µg of siRNA, respectively (FIGS. 14A and C). The NP/siRNA formulations did not significantly compromise cell survival showing more than 90% of viable cells 5 days post treatment at maximal NP dosages (FIGS. 14B and D).

Example 12

High Field Gradient Targeting of Magnetic Nanoparticle-Loaded Endothelial Cells to the Surface of Steel Stents Nanoparticle Formulation and Characterization. Magnetite prepared from ferric and ferrous chloride (300 mg and 150 mg, respectively) by alkaline precipitation with aqueous sodium hydroxide was magnetically separated, resuspended in 2 ml of ethanol and coated with oleic acid (200 mg) with heating under argon to 90° C. in a water bath for 5 min. Excess oleic acid was phase-separated by dropwise addition of 4 ml of water and the lipid-coated magnetite was washed twice with ethanol. Lipophilic magnetite was dispersed in 6 ml chloroform, forming a stable ferrofluid. The resulting organic dispersion of iron oxide was used to dissolve PLA, thus forming an organic phase. The organic phase was emulsified in an aqueous albumin solution (1%) by sonication in an ice bath followed by organic solvent evaporation. The particles were separated from the unbound albumin by repeated magnetic sedimentation/resuspension cycles, and lyophilized with 10% (w/v) glucose as a cryoprotectant. Lyophilized MNP were kept at −20° C. and resuspended in deionized water before use.

Particle size measurements were performed using the 90 Plus Particle Size Analyzer (Brookhaven Instruments, Holtville, N.Y. USA). The magnetic properties of MNP and cells loaded with MNP were estimated from the hysteresis curves of either MNP or MNP-loaded cells 5 µl samples air-dried on a 4×4 mm2 cover-glass slide using an alternating gradient magnetometer (Princeton Instruments Corporation, Princeton, N.J., USA).

Cell Preparation. Bovine aortic endothelial cells (BAEC) were seeded on clear-bottom 96-well plates at a density of $1.5 \times 10^4$ cells/well using DMEM supplemented with 10% fetal bovine serum (FBS) for the cell loading and cell viability experiments. To synchronize cell cultures with respect to MNP uptake, the cells were incubated at 4° C. for 30 min. Then MNP were added to cells at different doses and cell cultures were incubated on a magnetic separator adapted for cell culture plates using a magnetic field source of 500 Gauss (LifeSep™ 96F, Dexter Magnetic Technologies, Fremont, Calif., USA). Further, at predetermined time points cells were washed with phosphate buffered saline and the amount of internalized MNP was measured fluorimetrically ($\lambda$em/ $\lambda$ex=540/575 nm). Cell viability was determined at all time points using Calcein Green staining and the AlamarBlue assay as described by the manufacturer (Biosource, Camarillo, Calif. USA).

For the studies of in vitro cell capture on stents, BAEC were seeded on clear-bottom 12-well plates. On the next day 72 µg of MNP were added to each well of cells $(4.5 \pm 1.0) \times 10^4$. Cells and MNP were incubated on a magnetic source (Life Sep™ 96F) for 24 h to allow nearly complete (~95%) internalization of MNP. Then cells were trypsinized and resuspended in a cell culture medium for further capturing experiments. Cells used for in vivo delivery experiments were first transduced with replication defective type 5 (E1, E3 deleted) adenoviruses expressing luciferase (Ad luc) under the control of the human cytomegalovirus promoter (Gene Vector Core, University of Pennsylvania, Philadelphia, Pa.) for 10 hours (MOI=500) and then loaded with MNP for 24 hours.

In Vitro and In Vivo Short-Term Cell-Capture Experiments. In an in vitro cell capture experiment, MNP-loaded BAEC (ca. $2.5 \times 10^6$) circulated in a closed-loop system at a flow rate of 30 ml/min (0.015 m/s fluid velocity across the stent surface) while a homogeneous magnetic field of 1000 Gauss was applied. A homogeneous magnetic field was produced by passing an electrical current through serially connected solenoid coils with iron cores (40 mm in diameter) placed at both sides of either a stent positioned in a flow chamber of a model loop-circulatory system or a stented animal within a distance of 40 mm between the electromagnets' cores. An electrical current of 9.4 A was generated by a HP 6034A (Hewlett Packard, Palo Alto, Calif.) power supply by applying a voltage of 28V. The magnetic field strength was measured by a Hall Probe purchased from Lake Shore Cryotronics (Westerville, Ohio). Cell depletion was monitored by measuring MNP fluorescence and the results presented as a percent of captured cells.

In in vivo cell capture experiments 304 grade stainless steel stents were deployed in rat carotid arteries. For acute studies, BAEC cells preloaded with fluorescent MNP were transthoracically injected into the left ventricular cavity. Animals were exposed to a magnetic field of 1000 Gauss for 5 minutes, using the system described above, including the period of injection. Control rats underwent an identical procedure, where no magnetic field was employed. The animals were sacrificed 5 min after delivery, and the explanted stents were examined by fluorescence microscopy.

Angioplasty and In Vivo Delivery Procedure: 48-Hour Studies. The left common carotids of 450-500 g Sprague-Dawley male rats were injured by 4 passages of a Fogarty catheter prior to deployment (16 atm) of multilink stents made of 304 grade stainless steel (Circle Medical Devices, Los Gatos, Calif.). In the model studies of cell delivery under stop-flow conditions, a 23 G tubing was introduced via the external carotid into the common carotid artery and was positioned distal to the deployed stent. Thus, for these studies with temporary interruption of carotid blood flow, a 15 mm segment of common carotid artery encompassing the stented site was isolated by ligatures. The cell suspension (50 µl) was delivered into the isolated arterial segment for 15 sec, after which the excess cells that were not retained in the artery were evacuated by syringe retrieval. In the model studies of cell delivery under uninterrupted flow a 26 G tubing was introduced via the external carotid into the common carotid and advanced beyond the stent to the aortic arch (total 3.5 cm proximal from carotid bifurcation). The cells were injected at the rate 1 ml/min for one minute. For both delivery protocols, in the Mag+ group the injection was carried out with animals placed in a magnetic field of 1000 Gauss, as described above, and the field was maintained for a total of 5 minutes following delivery. In control rats (Mag-group) no magnetic field was applied. The animals were imaged 48 hours post delivery by local perivascular administration of 2.5 mg of luciferin admixed in 250 µl of 25% Pluronic F127 dissolved in PBS. This formulation undergoes phase transition between solution and gel at temperatures higher than 30° C. and thus immediately solidifies upon contact with tissue, forming a drug depot with well defined (24) rapid release kinetics. The imaging was initiated 5 minutes after delivery. The integration time was 10 min. For immunohistochemical detection of luciferase, paraformaldehyde-fixed cryoembedded arterial sections were stained with anti-luciferase mouse monoclonal antibody (Upstate-Millipore, Temacula, Calif., clone mAb21, 1:100) using a peroxidase/DAB method.

Statistics. Experimental data were presented as means±standard errors (SE). The results were evaluated by regression analysis. The Student t test was used to analyze the significance of differences in data sets. Differences were termed significant at $p<0.05$.

Figure 15A:
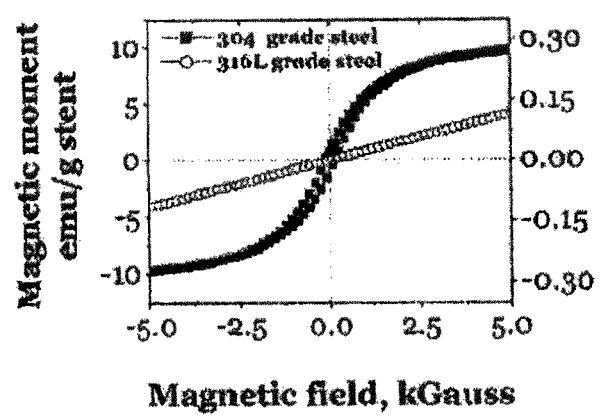
FIG. 15 shows the characterization of MNP and MNP-cell loading. 15A shows magnetization curves of 304 (left sided Y axis) and 316L (right sided Y axis) grade stainless steel stents. The 304 stainless steel stent exhibits a near superparamagnetic behavior showing slight hysteresis and a remnant magnetization on the order of 7% of the saturation magnetization value. By comparison, the 316L stent shows far less magnetic responsiveness. 15B shows micrographs of BAEC's in culture (magnification of ×100) with bright field and red fluorescent images qualitatively showing the relative amount of MNP internalized within cells at different time points at the applied MNP dose of 9 μg/well. Green fluorescent micrographs show cell viability as assessed by Calcein Green staining.

Results. Polylactide MNP were prepared by a modified emulsification-solvent evaporation methodology with the incorporation of oleate-coated iron oxide nanocrystals (Quintanar-Guerrero D et al. (1998) Drug Dev. Ind. Pharm. 24:1113-28) using bovine serum albumin (BSA) as a surface stabilizing agent. Albumin-stabilized MNP displayed a narrow size distribution with an average diameter of 290±15 nm (FIG. 11A) and exhibited superparamagnetic behavior showing no significant hysteresis, and a remnant magnetization on the order of 0.5% of the saturation magnetization value. The stent material used was 304 grade stainless steel, which was chosen for its combination of suitable magnetic properties and its corrosion resistance to aqueous environments. The 304 stents also exhibited nearly superparamagnetic behavior showing only slight magnetic hysteresis and displaying a remnant magnetization on the order of 7% of the saturation magnetization value (FIG. 15A). 316L stainless steel stents were also tested but were not included in targeting studies due to their less responsive magnetic properties (FIG. 15A).

Figure 15B:
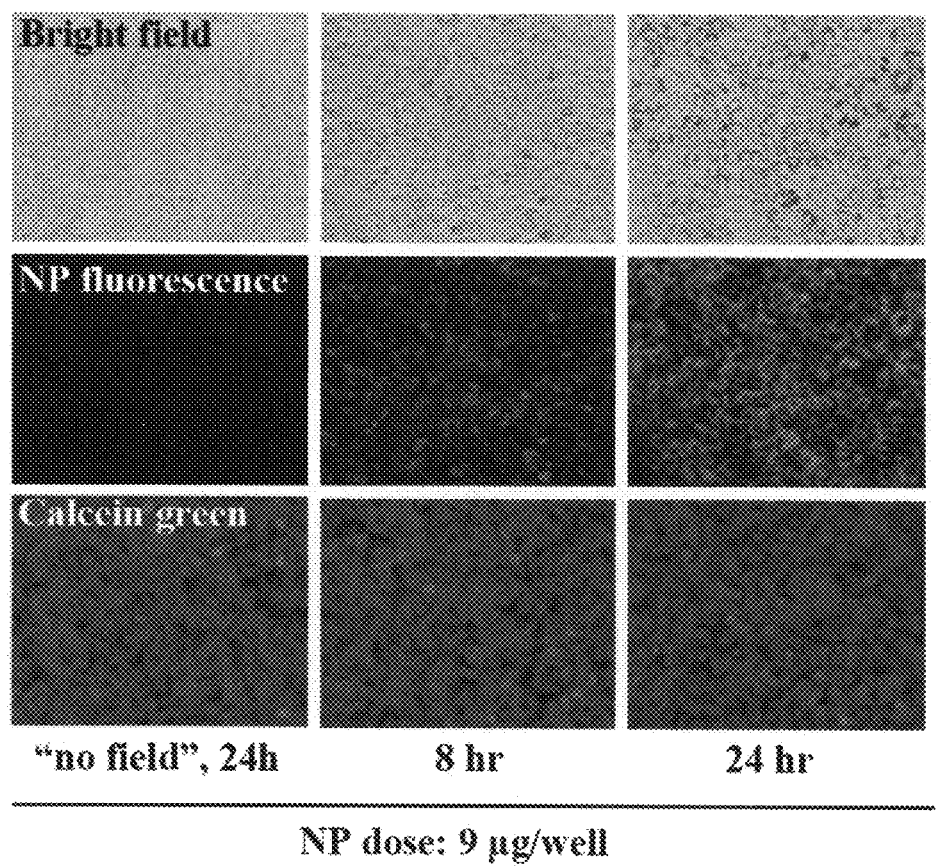

A subset of MNP were formulated with polylactic acid (PLA) that was covalently modified with BODIPY 564/570 thereby resulting in MNP that could be used in fluorescent microscopy experiments and fluorometry based quantitation studies (Chorny M et al. (2006) Mol. Ther. 14:382-91). This formulation was used to characterize the kinetics of cell loading with MNP. Bovine aortic endothelial cells (BAEC) in confluent cell cultures were incubated with various doses of BODIPY 564/570-MNP on a cell culture magnet (see Materials and Methods). The MNP uptake was determined at different time points by measuring the fluorescence of internalized nanoparticles. The amount of the internalized MNP was linearly dependent upon the MNP dose in the tested range (FIG. 12A). Approximately 30% of internalization was observed after 8 hours and the uptake was essentially complete after 24 hours (FIGS. 12A and 15B). Cell viability was not adversely affected by internalized MNP, as assessed by the results of Calcein Green staining and Alamar Blue assays (FIGS. 15B and 12B respectively). Cell survival of 83±3% relative to untreated cells was observed at the highest applied MNP dose, 9 µg/well (corresponding to a MNP loading of 0.3 ng/cell), and at the maximal incubation time of 24 hours (FIG. 12B). Based on these results, a MNP dose of 0.2 ng/cell was chosen for subsequent experiments (92±2% cell survival, a dose of 5.8 µg/well per FIG. 12B). As expected, BAEC laden with MNP demonstrated superparamagnetic behavior, showing hysteretic properties similar to free (non-cell associated) MNP (i.e., a remnant magnetization of less than 1% of the saturation value) (FIG. 15A).

Figure 16A:
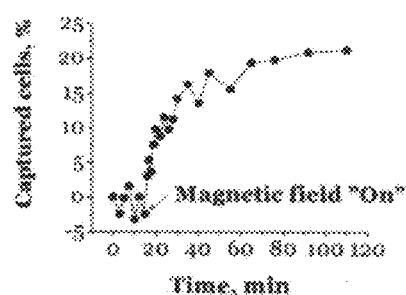
FIG. 16 shows magnetic targeting of MNP-preloaded BAEC under flow conditions in vitro and in vivo. 16A shows in vitro capture kinetics of magnetically responsive BAEC onto a 304 grade stainless steel stent in the presence of a uniform field of 1000 Gauss and a nonpulsatile flow with a rate of 30 ml/min. The initial capture rate was estimated to be 1% of cells/min. The data were obtained by measuring the fluorescence of internalized MNP. 16B and 16C show magnetically responsive BAEC captured in vitro onto a 304 stainless steel stent as evidenced by the red fluorescence of internalized MNP, or by Calcein Green staining of live cells, respectively. 16D shows MNP loaded BAEC captured in vivo onto a deployed 304 stainless steel stent in rat carotid artery. BAEC preloaded with fluorescent MNP were transthoracically injected into the left ventricular cavity. Animals were exposed to a magnetic field of 1000 Gauss for 5 minutes including the period of injection. The animals were sacrificed 5 minutes after delivery, and the explanted stents were immediately examined by fluorescence microscopy. 16E shows control rats subjected to an identical procedure, where no magnetic field was employed. Micrographs (b-e) were obtained at the magnification of ×40. 16F shows in vivo local magnetic cell delivery in a rat carotid stenting model under stop-flow conditions. A catheter was introduced via the external carotid into the common carotid artery and was positioned distal to a deployed stent. The cell suspension was delivered into isolated arterial segments for 15 sec. 16G shows in vivo cell delivery under uninterrupted blood flow conditions. A catheter was introduced via the external carotid into the common carotid and advanced beyond the stent to the aortic arch. The cells were injected at this site at the rate of 1 ml/min during one minute. For both delivery protocols (f and g), in the magnetic group (Mag+) the injection was carried out with animals placed in a magnetic field of 1000 Gauss, and the field was maintained for a total of 5 minutes following delivery. In control rats (Mag- group) no magnetic field was applied. In both settings BAEC were first transduced in culture with luciferase adenovirus and then loaded with MNP. The animals were imaged 48 hours post delivery by local perivascular administration of luciferin admixed in a Pluronic gel. The signal emitted from the stented arterial segment due to the luciferase transgene expression was significantly higher in the animals that received cells in the presence of a magnetic field (Mag+ group).
Figure 16B:

MNP-loaded endothelial cell targeting to 304 grade stainless steel stents was first studied in a model flow-loop system. In the absence of an externally applied uniform magnetic field, almost no cell capture was observed (FIG. 16A). However when a uniform magnetic field was applied across the stent within the flow loop system, the stent captured a significant percentage of the circulating cells, demonstrating an initial rate of 1% of cells captured per minute (FIG. 16A). Saturation in cell capture was observed within 50 min after the magnetic field was applied, resulting in the targeting of 20% of the circulating cells (ca. $0.5 \times 10^6$). Approximately 50% of the captured cells (ca. $0.25 \times 10^6$) accumulated on the stent surface within the first 6 minutes. FIG. 16B shows the stent surface at the end of the experiment with adherent cells completely covering the stent wire surfaces, as demonstrated by red MNP fluorescence microscopy results and Calcein Green staining indicating viability of the captured cells (FIG. 16C).

Figure 16D:
Figure 16C:
Figure 16E:

Acute rat carotid stenting studies were carried out by transthoracic injection of BAEC loaded with MNP into the left ventricular cavity in the presence of a uniform magnetic field (1000 Gauss) across the region of the stented artery (FIGS. 16D and E). The animals were euthanized 5 minutes after magnetic targeting, and the stents retrieved, revealing targeting of MNP to 304 grade stainless steel stent surfaces in the presence of a magnetic field (FIG. 16D), again with complete uniform coverage of the stent wires with cells containing fluorescent MNP. However, in the absence of a magnetic field, no detectable MNP-loaded BAEC were demonstrable (FIG. 16E). Thus, these short-term in vivo results were comparable to the in vitro targeting studies (FIG. 16B).

Figure 16F:
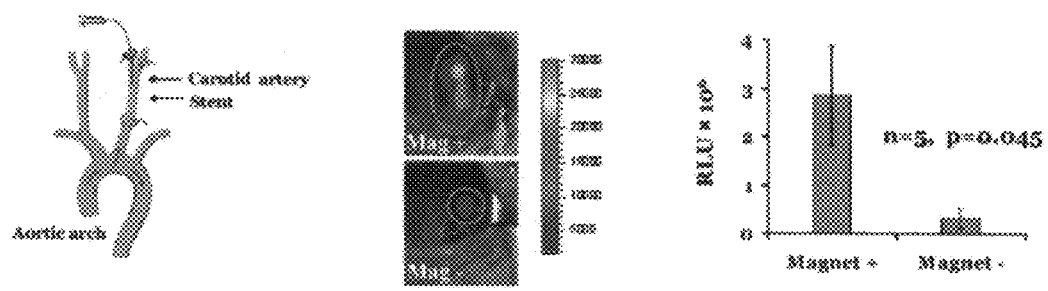

Experiments using BAEC both loaded with MNP and transduced with luciferase encoding replication defective adenoviruses (AdLuc) were carried out next. Initial studies examined magnetic targeting of MNP-loaded Luc modified BAEC with local delivery in a stop-flow setting (FIG. 16F), using Luc transgene activity as an endpoint, detected with intravital bioluminescence imaging (FIG. 16F). After in vitro AdLuc transduction and preloading with MNP, BAEC were harvested and locally delivered to an isolated stented segment of each rat's carotid artery in the presence or absence of a magnetic field (FIG. 16F). The stented vessel was temporarily tied off at both ends (stop-flow delivery technique) while the MNP-loaded BAEC were delivered to the stented section for a brief period of approximately 15 seconds (FIG. 16F). The cell suspension was then evacuated from the artery, and the magnetic field was maintained for an additional 5 minutes before the circulation was allowed to resume. The animals were recovered and studied 48 hours later, and as expected, significantly greater transgene expression (p=0.045) was demonstrated using local perivascular luciferin administration followed by bioluminescent in vivo optical imaging, in animals that had been administered with MNP-loaded BAEC in the presence of a uniform magnetic field compared to a control group not subjected to magnetic delivery conditions (FIG. 16F). It is also noteworthy that bioluminescent whole body imaging scans of the animals in these studies revealed an absence of transgene activity except within the stented carotid segments (data not shown).

Figure 16G:
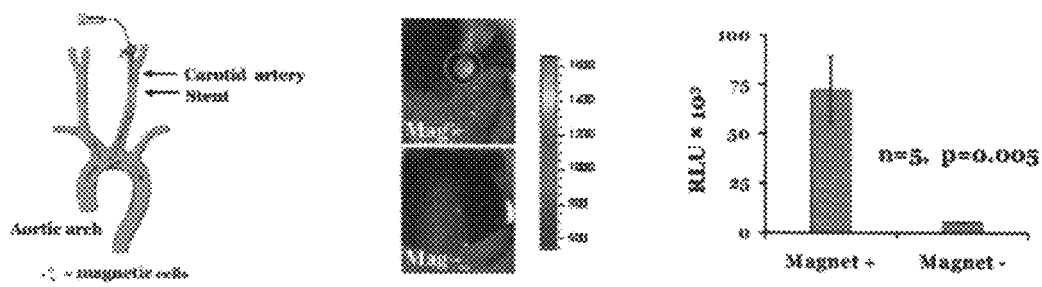

Magnetically targeted delivery of MNP-loaded BAEC without interruption of the stented carotid blood flow was also investigated by injecting the MNP-loaded BAEC expressing Luc over the course of 1 minute through a catheter positioned in the aortic arch with exposure to a uniform magnetic field for 5 minutes (FIG. 16G). Specific targeting to the deployed stents due to the applied field was demonstrated after 48 hours by bioluminescent imaging (FIG. 16G), with no detectable Luc activity present in stented arterial segments that were not exposed to a magnetic field (p=0.005). Furthermore, there was an absence of bioluminescence in distal sites (data not shown) in these studies as well. Luc-positive immunostaining confirmed the presence of transgene activity in the intimal and medial regions of the stented arterial segments that were exposed to magnetic cell targeting (data not shown).

Example 13

Use of a MRI Homogenous Magnetic Field to Target Magnetic Nanoparticle-Loaded Cells to a 316L Stent A model experiment was carried out to demonstrate the feasibility of targeting cells loaded with magnetic nanoparticles (MNP) to steel stents using the homogeneous magnetic field present in a magnetic resonance imaging (MRI) system. The field present in the imager, 1.5 Tesla (T) is 15-fold greater than the highest fields used in other studies (1000 Gauss, or 0.1 Tesla). Furthermore, prior studies used 304 steel stents that were magnetized in a 0.1 Tesla field, whereas 316L steel stents were not magnetized at this level of field strength. Furthermore, it should be noted that the majority of steel stents used today clinically are 316L steel, and thus this model experiment is particularly clinically relevant.

Figure 17:
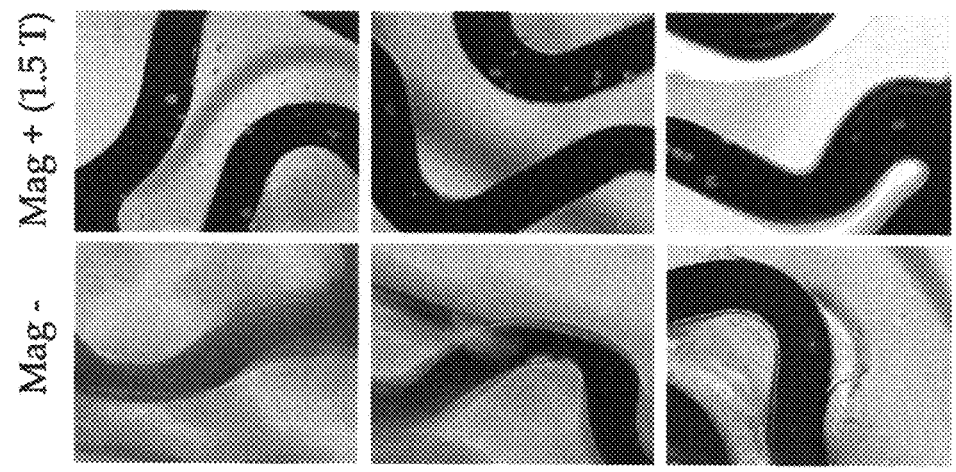
FIG. 17 shows that a MRI imager can magnetize a 316L steel stent for cell targeting. In the presence of a magnetic field (Mag+), BAECs preloaded with red fluorescent polylactic acid (PLA) MNP are shown to localize to the magnetized steel stent. Controls (Mag-) did not show a significant localization to the stent.

The experiment was carried out as follows: Bovine arterial endothelial cells (BAEC) were preloaded with red fluorescent polylactic acid (PLA) MNP prepared as described above on day −1. The cells were trypsinized, resuspended in 5 ml of cell culture medium (DMEM supplemented with 10% FBS) before the experiment, and divided in two halves. Stainless steel 316 grade stents (Crown, Cordis, Warrenton, N.J.) were deployed in flexible polyvinylchloride tubes, to simulate arterial deployment, attached to syringes. The cell suspension was extruded from the syringe through the tube with the stent within it over a 1 min period (collecting the cell suspension in the 2nd syringe) with or without an exposure to a homogenous magnetic field (1.5 Tesla) within the core of a MRI imager. The stents were imaged by fluorescent microscopy using an inverted fluorescent microscope immediately after the experiment before and after stent removal from the tubes. The results shown in FIG. 17 demonstrate red fluorescent cells present on all of the 316L stent struts of the stent samples that were exposed to the 1.5 T field. However, the control stent, which had cells (plus fluorescent MNP) injected through the stented polyvinylchloride tubing demonstrated only rare red fluorescent cells. Thus, these studies demonstrate that the homogenous field present within a MRI imager can magnetize a 316L stent and thereby enable magnetic cell targeting. These results show that MNP targeting by simply injecting a suspension of MNP (without loading them into cells), would also target a 316L stent in the 1.5 T field.

Example 14

Superparamagnetic Polymeric Nanoparticles Efficiently Enhance Non-Viral Nucleic Acid Delivery Non-viral delivery of nucleic acids for therapeutic purposes remains a challenge mainly due to a comparatively low efficacy. We addressed this problem by using non-viral gene carriers possessing magnetic targeting properties. The achievable via magnetic force targeted delivery of nucleic acids may provide a clinically viable solution for effective and non-toxic gene transfer. In our previous work we developed formulations of polylactide (PLA)-based biodegradable nanoparticles (NP) surface modified with branched polyethylenimine (PEI 25K). Recent scientific literature showed that deacylation of commercial preparations of linear PEI dramatically boosted its gene delivery efficiency due to increase in the number of protonatable nitrogens, which presumably results in a tighter condensation of nucleic acid and a better endosomal escape of the PEI/nucleic acid complexes. The present studies investigated the hypothesis that non-viral gene transfer can be enhanced via magnetically driven delivery of superparamagnetic NP formulated with deacylated linear PEI. The linear PEI synthesized by acid-catalyzed hydrolysis of 200-kDa poly(2-ethyl-2-oxazoline) and adjusted to pH7 was used to formulate iron oxide laden NP by means of modified emulsification-solvent evaporation methodology. NP containing 35% iron oxide by weight had an average size of 360±25 nm, zeta-potential of 43±3 mV and exhibited superparamagnetic properties (magnetic remnance less than 0.5% of their magnetic saturation value). The ability of linear PEI-NP formulation to deliver nucleic acids was examined in vitro in cultured A10, rat aortic smooth muscle cells (SMC) and bovine aortic endothelial cells (BAEC), using green fluorescent protein (GFP) as a reporter gene. NP formulated with branched PEI were used for comparison. NP complexed with nucleic acids were applied to cells for 15 min under magnetic field (500 G) in serum-containing cell culture medium. In one set of experiments, GFP encoding plasmid DNA was delivered to the cells and the transfection efficiency was measured fluorimetrically 2, 4 and 8 days post treatment. Intracellular NP levels were directly dose dependent in examined NP concentration range for both PEI formulations. The GFP expression reached its maximal level for both PEI formulations at day 4 resulting in 2.5-3 times higher GFP levels for both cell types transfected with linear PEI-NP formulation. In another set of experiments, enhanced GFP (eGFP) short interfering RNA (siRNA) was delivered to the cells and the suppression of eGFP expression in lentivirus transduced smooth muscle and endothelial cells as well as cell viability (by AlamarBlue) were measured fluorimetrically 5 days post treatment. In GFP silencing experiments, efficient eGFP suppression was achieved using magnetic NP formulated with either branched or linear PEI. The eGFP suppression in A10 cells depended directly on the NP dose for both formulation types. The suppression of eGFP was directly siRNA dose dependent in the case of linear PEI-NP and inversely dependent for branched PEI-NP resulting in a maximal suppression of 40% for both NP types. In BAEC, the eGFP suppression depended directly on the NP dose for the branched PEI-NP only. The eGFP suppression was not dependent on the siRNA doses for both NP types resulting in a maximal suppression of 50% for both NP formulations. Studied NP/siRNA complexes did not significantly compromise cell survival showing more than 90% of viable cells 5 days post treatment at maximal NP dosages for both NP and cell types. It is concluded that magnetically responsive linear PEI-NP demonstrated increased delivery efficiency of plasmid DNA versus branched PEI-NP while in the gene silencing experiments no difference in capacity to suppress genes for both types of NP was observed.

The present invention is not limited to the embodiments described and exemplified above, but is capable of variation and modification within the scope of the appended claims.

What is claimed is:

1. A system for magnetically targeting therapeutic particles comprising:
   (a) at least one particle comprising at least one therapeutic agent and a first magnetic or magnetizable material;
   (b) an implantable device comprising a second magnetic or magnetizable material;
   and,
   (c) a magnetic field generator comprising first and second magnets configured and operable to generate a uniform magnetic field across the implantable device capable of magnetizing magnetizable material and directing the at least one particle to the device,
   wherein the magnetic field generator is configured such that the uniform magnetic field generates at least one directable magnetic field gradient, the gradient directing the at least one particle to the device.

2. The system of claim 1, wherein the gradient is generated proximal to the device.

3. The system of claim 1, wherein the at least one therapeutic agent comprises a pharmaceutical, biomolecule, or cell.

4. The system of claim 3, wherein the biomolecule is a nucleic acid.

5. The system of claim 4, wherein the nucleic acid is a regulatory nucleic acid.

6. The system of claim 5, wherein the regulatory nucleic acid is siRNA, shRNA, or miRNA.

7. The system of claim 3, wherein at least one therapeutic agent is an endothelial cell.

8. The system of claim 7, wherein the endothelial cell is a vascular endothelium cell.

9. The system of claim 1, wherein the implantable device is a stent.

10. The system of claim 1, wherein the implantable device is formed of grade 304 stainless steel.

11. The system of claim 1, wherein a surface of the at least one particle is modified to prolong bioavailability.

12. The system of claim 1, wherein the first and second magnets are electromagnets.

13. The system of claim 12, wherein the electromagnets are portable for selective arrangement and placement relative to a subject.

14. The system of claim 1, wherein at least one of said first and second magnets comprises a permanent magnet.

15. The system of claim 1, wherein the at least one particle comprises a plurality of nanoparticles.

16. The system of claim 1, wherein the at least one particle comprises a polylactic acid (PLA) matrix.

17. The system of claim 1, wherein the at least one particle comprises magnetite.

18. The system of claim 1, wherein the at least one therapeutic agent comprises paclitaxel.

19. The system of claim 1, wherein the at least one particle comprises a plurality of particles, and the system further comprises a retrieval system, the retrieval system operable to capture one or more of said plurality of particles that are not delivered to the implantable device.

20. A method for magnetically targeting a therapeutic agent to a device implanted in a subject, the implanted device comprising a first magnetic or magnetizable material, the method comprising the steps of:
   (a) administering at least one particle to the subject, the at least one particle comprising the therapeutic agent and a second magnetic or magnetizable material;
   (b) generating across the implanted device a uniform magnetic field capable of magnetizing magnetizable materials, wherein the uniform magnetic field is provided by a magnetic field generator comprising first and second magnets and wherein the uniform magnetic field generates a magnetic field gradient proximal to the implanted device; and
   (c) targeting the at least one particle to the implanted device under the magnetic field gradient, wherein the magnetic field gradient targets the particle to the implanted device;
   wherein the step of generating a uniform magnetic field comprises a step of selectively placing the first and second magnets around the subject to direct said uniform magnetic field through said implanted device.

21. The method of claim 20, wherein the step of administering at least one particle to the subject comprises a step of administering a plurality of particles to the subject.

22. The method of claim 21 further comprising a step of removing one or more of said plurality of particles from the subject that are not delivered to the implanted device.

23. The method of claim 20, wherein the therapeutic agent is a pharmaceutical, biomolecule, or cell.

24. The method of claim 23, wherein the therapeutic agent is a biomolecule, and the biomolecule is a nucleic acid.

25. The method of claim 24, wherein the nucleic acid is a regulatory nucleic acid.

26. The method of claim 25, wherein the regulatory nucleic acid is siRNA, shRNA, or miRNA.

27. The method of claim 23, wherein the at least one therapeutic agent is an endothelial cell.

28. The method of claim 27, wherein the endothelial cell is a vascular endothelium cell.

29. The method of claim 20, wherein the implanted device is a stent.

30. The method of claim 20, wherein the implanted device is located in a peripheral artery of a subject.

31. The method of claim 20, wherein the implanted device comprises grade 304 stainless steel.

32. The method of claim 20, wherein the step of generating a uniform magnetic field is performed after the step of administering at least one particle to the subject.

33. The method of claim 20, wherein the therapeutic agent comprises paclitaxel.

34. The method of claim 20, further comprising a step of repeating steps (a), (b) and (c) to deliver an additional quantity of said therapeutic agent to the implanted device.

35. The method of claim 20, wherein at least one of said first and second magnets is a permanent magnet and wherein the step of generating a uniform magnetic field comprises a step of using the permanent magnet to direct said uniform magnetic field through said implanted device.

\* \* \* \* \*